United States Patent
Jang et al.

(10) Patent No.: US 8,513,028 B2
(45) Date of Patent: Aug. 20, 2013

(54) USE OF MLN51 GENE AND PROTEIN

(75) Inventors: Jin Ah Jang, Jeollanam-do (KR); Dae Seog Lim, Gyeonggi-do (KR); Hyun Soo Lee, Seoul (KR); Yong Soo Bae, Gyeonggi-do (KR)

(73) Assignee: Creagene Inc., Kyungki-do (KR)

( * ) Notice: Subject to any disclaimer, the term of this patent is extended or adjusted under 35 U.S.C. 154(b) by 944 days.

(21) Appl. No.: 12/299,919

(22) PCT Filed: May 8, 2007

(86) PCT No.: PCT/KR2007/002259
§ 371 (c)(1),
(2), (4) Date: Nov. 7, 2008

(87) PCT Pub. No.: WO2007/129858
PCT Pub. Date: Nov. 15, 2007

(65) Prior Publication Data
US 2009/0131361 A1      May 21, 2009

(30) Foreign Application Priority Data

May 9, 2006     (KR) .................. 10-2006-0041646

(51) Int. Cl.
*C12Q 1/68* (2006.01)
*G01N 33/53* (2006.01)
*G01N 33/543* (2006.01)
*G01N 33/544* (2006.01)
*G01N 33/567* (2006.01)
*G01N 33/574* (2006.01)
*A61K 31/70* (2006.01)
*A61K 39/395* (2006.01)
*C07K 16/18* (2006.01)
*C12P 21/08* (2006.01)

(52) U.S. Cl.
USPC .............. 436/503; 424/138.1; 424/152.1; 424/173.1; 424/174.1; 435/6.1; 435/6.12; 435/6.13; 435/7.1; 435/7.2; 435/7.21; 435/7.23; 435/7.24; 435/7.8; 435/40.5; 435/40.51; 435/40.52; 436/514; 436/518; 436/528; 436/530; 436/63; 436/811; 514/44 A; 530/388.7; 530/388.8; 530/389.6; 530/389.7

(58) Field of Classification Search
USPC ............... 435/6, 7.2, 7.21, 7.23, 7.24, 7.4, 435/7.8, 40.5, 40.51, 40.52, 6.1, 6.12, 6.13, 435/7.1; 436/503, 514, 518, 528, 530, 63, 436/811; 530/388.7, 388.8, 388.25, 389.6, 530/389.7; 424/130.1, 138.1, 145.1, 152.1, 424/158.1, 173.1, 174.1; 514/44, 44 A, 44 R
See application file for complete search history.

(56) References Cited

U.S. PATENT DOCUMENTS
2004/0018525 A1 *   1/2004   Wirtz et al. ................ 435/6

FOREIGN PATENT DOCUMENTS
WO          02/28999     *   4/2002
WO       2004/072277     *   8/2004

OTHER PUBLICATIONS

Clayton, 2004. The silent treatment. Nature 431: 599, 601, 603, and 605.*
Oh et al., 2009. siRNA delivery systems for cancer treatment. Advanced Drug Delivery Reviews 61: 850-862.*
Degot et al., "Metastatic Lymph Node 51, a Novel Nucleo-Cytoplasmic Protein Overexpressed in Breast Cancer," Oncogene 21:4422-4434, 2002.
Degot et al., "Association of the Breast Cancer Protein MLN51 with the Exon Junction Complex Via its Speckle Localizer and RNA Binding Module," J. Biol. Chem. 279:33702-33715, 2004.
Jang et al., "MLN51 and GM-CSF Involvement in the Proliferation of Fibroblast-like Synoviocytes in the Pathogenesis of Rheumatoid Arthritis," Arthritis Research and Therapy 8:R170, 2006.
Uchida et al., "Application of a Novel Protein Biochip Technology for Detection and Identification of Rheumatoid Arthritis Biomarkers in Synovial Fluid," J. Proteome Res. 1:495-499, 2002.
International Search Report from International Application No. PCT/KR2007/002259, dated Aug. 20, 2007.

* cited by examiner

*Primary Examiner* — Mark Shibuya
*Assistant Examiner* — James L Grun
(74) *Attorney, Agent, or Firm* — Clark & Elbing LLP

(57) ABSTRACT

The present invention relates to novel uses of the MLN 51 gene or protein. The MLN 51 gene and protein is closely related to the development of rheumatoid arthritis and serve as biomarker and therapeutic target for rheumatoid arthritis, particularly chronic synovitis.

4 Claims, 8 Drawing Sheets

US 8,513,028 B2

USE OF MLN51 GENE AND PROTEIN

CROSS-REFERENCE TO RELATED APPLICATIONS

This application claims priority under 35 U.S.C. §371 from international application PCT/KR2007/002259, filed May 8, 2007, which claims priority from Korean Patent Application 10-2006-0041646, filed May 9, 2006.

BACKGROUND OF THE INVENTION

1. Field of the Invention

The present invention relates to novel uses of the MLN 51 gene or protein, in particular, to novel uses of the MLN 51 gene or protein associated with rheumatoid arthritis.

2. Description of the Related Art

Synovial tissue from healthy individuals consists of a single layer of synovial cells without infiltration of inflammatory cells. In synovial tissue of rheumatoid arthritis (RA) patients, lymphocytes and macrophages are recruited and activated, and these activated macrophages release high concentrations of inflammatory cytokines. In response to these cytokines, synovial fibroblasts proliferate vigorously and form villous hyperplastic synovial tissues. These fibroblasts secrete inflammatory mediators, which further attract inflammatory cells and stimulate growth of the synovial fibroblasts as well as that of vascular endothelial cells (1). These activated macrophages and fibroblasts produce tissue-degrading proteinases (2). Thus, the invasive hyperplastic synovial tissue, termed pannus, is directly responsible for structural and functional damage of the affected joints. Therapeutic intervention against RA could be aimed at any one of these steps, but the underlying mechanisms for this are largely unknown. Impaired regulation of apoptosis has been associated with RA (3-5). Recently, however, apoptotsis of synovial cells has been identified in rheumatoid synovium (6,7), suggesting that synovial tissue hyperplasia may be a result of cell proliferation rather than that of apoptotic cell death.

Throughout this application, various patents and publications are referenced and citations are provided in parentheses. The disclosures of these patents and publications in their entities are hereby incorporated by reference into this application in order to more fully describe this invention and the state of the art to which this invention pertains.

DETAILED DESCRIPTION OF THIS INVENTION

The present inventors have done intensive research to develop novel biomarkers or therapeutic targets relating to pathogenesis of rheumatoid arthritis (RA), and as a result found that MLN 51 (metastatic lymph node 51) plays a crucial role in RA pathogenesis.

Accordingly, it is an object of this invention to provide a kit for detecting rheumatoid arthritis.

It is another object of this invention to provide a method for screening a substance for preventing or treating rheumatoid arthritis.

It is still another object of this invention to provide a pharmaceutical composition for preventing or treating rheumatoid arthritis.

It is further an object of this invention to provide a rheumatoid arthritis-related biomarker.

It is still further an object of this invention to provide a method for detecting rheumatoid arthritis.

It is still yet further an object of this invention to provide a method for preventing or treating rheumatoid arthritis.

It is another object of this invention to provide a use of a primer or probe having a nucleotide sequence complementary to the nucleotide sequence of the MLN 51 (metastatic lymph node 51) gene as set forth in SEQ ID NO:1 for manufacturing a composition for detecting rheumatoid arthritis.

It is still another object of this invention to provide a use of an antibody binding specifically to the MLN 51 (metastatic lymph node 51) protein as set forth in SEQ ID NO:2 for manufacturing a composition for detecting rheumatoid arthritis.

It is a further object of this invention to provide a use of a substance to inhibit the expression of the MLN 51 (metastatic lymph node 51) gene or the activity of the MLN 51 protein for manufacturing a medicament for detecting, preventing, or treating rheumatoid arthritis.

Other objects and advantages of the present invention will become apparent from the following detailed description together with the appended claims and drawings.

In one aspect of this invention, there is provided a kit for detecting rheumatoid arthritis, which comprises a primer or probe having a nucleotide sequence complementary to the nucleotide sequence of the MLN 51 (metastatic lymph node 51) gene as set forth in SEQ ID NO:1.

In another aspect of this invention, there is provided a kit for detecting rheumatoid arthritis, which comprises an antibody that specifically binds to the MLN 51 protein as set forth in SEQ ID NO:2.

In still another aspect of this invention, there is provided a method for detecting rheumatoid arthritis, which comprises contacting a nucleic acid sample with a probe having a nucleotide sequence complementary to the nucleotide sequence of the MLN 51 (metastatic lymph node 51) gene as set forth in SEQ ID NO:1.

In a further aspect of this invention, there is provided a method for detecting rheumatoid arthritis, which comprises amplifying a nucleic acid sample by use of a primer having a nucleotide sequence complementary to the nucleotide sequence of the MLN 51 (metastatic lymph node 51) gene as set forth in SEQ ID NO:1.

In still a further aspect of this invention, there is provided a method for detecting rheumatoid arthritis, which comprises contacting a biosample with an antibody that specifically binds to the MLN 51 (metastatic lymph node 51) protein as set forth in SEQ ID NO:2.

In still yet a further aspect of this invention, there is provided a use of a primer or probe having a nucleotide sequence complementary to the nucleotide sequence of the MLN 51 (metastatic lymph node 51) gene as set forth in SEQ ID NO:1 for manufacturing a composition for detecting rheumatoid arthritis.

In another aspect of this invention, there is provided a use of an antibody that specifically binds to the MLN 51 (metastatic lymph node 51) protein as set forth in SEQ ID NO:2 for manufacturing a composition for detecting rheumatoid arthritis.

The present inventors have done intensive research to develop novel biomarkers relating to pathogenesis of rheumatoid arthritis (RA), and as a result found that MLN 51 (metastatic lymph node 51) plays a crucial role in RA pathogenesis, particularly in chronic synovitis of RA patients.

MLN 51 (metastatic lymph node 51) was first identified in breast cancer cells (8, 9). Early studies revealed that MLN 51 plays an essential role in mRNA trafficking from the nucleus to the cytoplasm (10-12). Recently, its localization, RNA binding module, structural analysis and biological functions were addressed in several reports (8-12).

The present invention is drawn to novel uses of MLN 51, in particular to novel uses of MLN 51 as diagnostic or therapeutic targets for rheumatoid arthritis. The novel use of the present invention is based on our findings that MLN 51 is closely associated with hyperproliferation of RA FLS (rheumatoid arthritis fibroblast-like synoviocytes).

RA is a heterogeneous autoimmune disease. Histologically, RA joints are characterized by chronic inflammation with hyperplasia of the synovial lining cells. It is now well established that FLS (fibroblast-like synoviocytes) actively participate in RA synovitis. FLS in RA joints aggressively proliferate to form a pannus, which eventually destroys articular bone and cartilage. A number of growth factors or cytokines have been described in association with the proliferative response of FLS, such as TGF-β, PDGF, fibroblast growth factor, IL-1β, TNF-α, and IL-6. However, in trials of those therapeutic agents, response was not achieved in a significant proportion of patients, suggesting that some other important factors still remain undiscovered. To the best of our knowledge, the present invention is the first report or suggestion that MLN 51 plays a critical role in hyperproliferation of RA FLS.

The probes or primers used in the present kit have a complementary sequence to the nucleotide sequence of the MLN 51 (metastatic lymph node 51) gene as set forth in SEQ ID NO:1. The term "complementary" with reference to a sequence used herein refers to a sequence having complementarity to the extent that the sequence anneals or hybridizes specifically with the nucleotide sequence of the MLN 51 gene set forth in SEQ ID NO:1 under certain annealing or hybridization conditions. In this regard, the term "complementary" used herein has a different meaning from the term "perfectly complementary". The probes or primers used in the present invention can have one or more mismatch, so long as such mismatches are not sufficient to completely preclude specific annealing or hybridization to the MLN 51 gene.

As used herein the term "probe" means a linear oligomer of natural or modified monomers or linkages, including deoxyribonucleotides and ribonucleotides, capable of specifically binding to a target polynucleotide. The probe may be naturally occurring or artificially synthesized. The probe is preferably single stranded. Preferably, the probes used in the present invention are oligodeoxyribonucleotides. The probe of this invention can be comprised of naturally occurring dNMP (i.e., dAMP, dGMP, dCMP and dTMP), modified nucleotides, or non-natural nucleotides. The primer can also include ribonucleotides. For instance, the probes of this invention may include nucleotides with backbone modifications such as peptide nucleic acid (PNA) (M. Egholm et al., *Nature,* 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-, inosine, and diaminopurine.

The term "primer" as used herein refers to an oligonucleotide, which is capable of acting as a point of initiation of synthesis when placed under conditions in which synthesis of a primer extension product which is complementary to a nucleic acid strand (template) is induced, i.e., in the presence of nucleotides and an agent for polymerization, such as DNA polymerase, and at a suitable temperature and pH. The suitable length of primers will depend on many factors, including temperature, application and source of primer, generally, 15-30 nucleotides in length. Shorter primers generally need a lower temperature to form stable hybridization duplexes with templates.

The sequences of primers are not required to be perfectly complementary to sequences of templates. The sequences of primers may comprise some mismatches, so long as they can be hybridized with templates and serve as primers. Therefore, the primers of this invention are not required to be perfectly complementary to sequences of the MLN 51 gene as a template; it is sufficient that they have complementarity to the extent that they anneal specifically to the nucleotide sequence of the MLN 51 gene for acting as a point of initiation of synthesis. The primer design may be conveniently performed with referring to the MLN 51 gDNA or cDNA sequences, preferably, cDNA sequence. For instance, the primer design may be carried out using computer programs for primer design (e.g., PRIMER 3 program). Exemplified primers of this invention are set forth in SEQ ID NO:3 (sense primer) and SEQ ID NO:4 (antisense primer).

According to a preferred embodiment, the diagnosis or detection kit for rheumatoid arthritis comprising probes is in the form of a microarray, more preferably a DNA or cDNA microarray, most preferably a cDNA microarray.

In a microarray, the present probes serve as hybridizable array elements and are immobilized on substrates. A preferable substrate includes suitable solid or semi-solid supporters, such as a membrane, filter, chip, slide, wafer, fiber, magnetic or nonmagnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements are bound to a glass surface modified to contain epoxi compound or aldehyde group or to a polylysin-coated surface. Further, the hybridizable array elements are bound to a substrate through linkers (e.g. ethylene glycol oligomer and diamine).

DNAs to be examined with a microarray of this invention may be labeled, and hybridized with array elements on microarray. Various hybridization conditions are applicable, and for the detection and analysis of the extent of hybridization, various methods are available depending on labels used.

The present method for diagnosing rheumatoid arthritis may be carried out in accordance with hybridization. For such analysis, probes, which have a complementary sequence to the nucleotide sequence of the MLN 51 (metastatic lymph node 51) gene as set forth in SEQ ID NO:1, are used.

Using probes hybridizable with the MLN 51 gene or cDNA, preferably cDNA, rheumatoid arthritis is diagnosed or detected by a hybridization-based assay. According to a preferred embodiment, some modifications in the probes of this invention can be made unless the modifications abolish the advantages of the probes. Such modifications, i.e., labels linked to the probes, generate a signal to detect hybridization. Suitable labels include but are not limited to fluorophores (e.g., fluorescein), phycoerythrin, rhodamine, lissamine, Cy3 and Cy5 (Pharmacia), chromophores, chemiluminescers, magnetic particles, radioisotopes (e.g., $P^{32}$ and $S^{35}$), mass labels, electron dense particles, enzymes (e.g., alkaline phosphatase and horseradish peroxidase), cofactors, substrates for enzymes, heavy metals (e.g., gold), and haptens having specific binding partners, e.g., an antibody, streptavidin, biotin, digoxigenin and chelating group. Labeling is performed according to various methods known in the art, such as nick translation, random priming (Multiprime DNA labeling systems booklet, "Amersham" (1989)) and kination (Maxam & Gilbert, *Methods in Enzymology*, 65:499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

The nucleic acid sample (preferably, cDNA) to be analyzed may be prepared using mRNA from various biosamples. The biosample is preferably a cell from synovial tissues, most preferably FLS (fibroblast-like synoviocyte). Instead of probes, cDNA may be labeled for hybridization-based analysis.

Probes are hybridized with cDNA molecules under stringent conditions for detecting rheumatoid arthritis. Suitable hybridization conditions may be routinely determined by optimization procedures. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999). For example, high stringency conditions include hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, high stringency conditions include washing in 6×SSC/0.05% sodium pyrophosphate at 48° C. Low stringency conditions include, e.g., washing in 0.2×SSC/0.1% SDS at 42° C.

Following hybridization reactions, a hybridization signal indicative of the occurrence of hybridization is then measured. The hybridization signal may be analyzed by a variety of methods depending on the labels. For example, where probes are labeled with enzymes, the occurrence of hybridization may be detected by reacting substrates for the enzymes with the hybridization products. Enzyme substrate pairs useful in this invention include, but are not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine; a pair of alkaline phosphatase and bromochloroindolylphosphate (BCIP), nitro blue tetrazolium (NBT), naphthol-AS-B1-phosphate or ECF substrate; and a pair of glucosidase and t-NBT (nitroblue tetrazolium) or m-PMS (phenzaine methosulfate). Where probes are labeled with gold particles, the occurrence of hybridization may be detected by a silver staining method using silver nitrate.

In these instances, where the present method for diagnosing rheumatoid arthritis is carried out by hybridization, it comprises the steps of (i) contacting a nucleic acid sample with a probe having a nucleotide sequence complementary to the nucleotide sequence of the MLN 51 (metastatic lymph node 51) gene as set forth in SEQ ID NO:1; and (ii) detecting the occurrence of hybridization.

The signal intensity from hybridization is indicative of rheumatoid arthritis. When the hybridization signal to MLN 51 cDNA from a sample to be diagnosed is measured to be stronger than normal samples (or osteoarthritis samples), the sample can be determined to indicate rheumatoid arthritis.

According to a preferred embodiment, the primers of this invention are used for amplification reactions.

The term used herein "amplification reactions" refers to reactions for amplifying nucleic acid molecules. A multitude of amplification reactions have been suggested in the art, including but not limited to polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., *Molecular Cloning. A Laboratory Manual*, 3rd ed. Cold Spring Harbor Press (2001)), the methods of Miller, H. I. (WO 89/06700) and Davey, C. et al. (EP 329,822), ligase chain reaction (LCR)(17, 18), Gap-LCR (WO 90/01069), repair chain reaction (EP 439,182), transcription-mediated amplification (TMA)(19) (WO 88/10315), self sustained sequence replication (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), strand displacement amplification and loop-mediated isothermal amplification (LAMP). Other amplification methods that may be used are described in U.S. Pat. Nos. 5,242,794, 5,494,810, 4,988,617 and in U.S. Ser. No. 09/854,317.

According to the most preferred embodiment, the amplification reaction is carried out in accordance with PCR (polymerase chain reaction) which is disclosed in U.S. Pat. Nos. 4,683,195, 4,683,202, and 4,800,159.

PCR is one of the most predominant processes for nucleic acid amplification and a number of variations and applications have been developed. For example, for improving PCR specificity or sensitivity, touchdown PCR(24), hot start PCR (25, 26), nested PCR(2) and booster PCR(27) have been developed by modifying traditional PCR procedures. In addition, real-time PCR, differential display PCR (DD-PCR), rapid amplification of cDNA ends (RACE), multiplex PCR, inverse polymerase chain reaction (IPCR), vectorette PCR, thermal asymmetric interlaced PCR (TAIL-PCR) and multiplex PCR have been suggested for certain applications. The details of PCR can be found in McPherson, M. J., and Moller, S. G. PCR. BIOS Scientific Publishers, Springer-Verlag New York Berlin Heidelberg, N.Y. (2000), the teachings of which are incorporated herein by reference in its entity.

Where the present method for diagnosing rheumatoid arthritis is carried out using primers, nucleic acid amplification is executed for analyzing the expression level of the MLN 51 gene. Because the present invention is intended to assess the expression level of the MLN 51 gene, the level of the MLN 51 mRNA in samples (e.g., FLS) is analyzed.

Therefore, the present invention performs nucleic acid amplifications using mRNA molecules in samples as templates and primers to be annealed to mRNA or cDNA.

For obtaining mRNA molecules, total RNA is isolated from samples. The isolation of total RNA may be performed by various methods (Sambrook, J. et al., *Molecular Cloning. A Laboratory Manual*, 3rd ed. Cold Spring Harbor Press (2001); Tesniere, C. et al., *Plant Mol. Biol. Rep.*, 9:242 (1991); Ausubel, F. M. et al., *Current Protocols in Molecular Biology*, John Willey & Sons (1987); and Chomczynski, P. et al., *Anal. Biochem.* 162:156 (1987)). For example, total RNA in cells may be isolated using Trizol. Afterwards, cDNA molecules are synthesized using mRNA molecules, isolated, and then amplified. Since total RNA molecules used in the present invention are isolated from human samples, mRNA molecules have poly-A tails and are converted to cDNA by use of a dT primer and reverse transcriptase (*PNAS USA*, 85:8998 (1988); Libert F, et al., *Science*, 244:569 (1989); and Sambrook, J. et al., *Molecular Cloning. A Laboratory Manual*, 3rd ed. Cold Spring Harbor Press (2001)). cDNA molecules synthesized are then amplified by amplification reactions.

The primers used for the present invention are hybridized or annealed to a region on the template so that a double-stranded structure is formed. Conditions of nucleic acid hybridization suitable for forming such double stranded structures are described by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase such as may be obtained from a variety of bacterial species, including *Thermus aquaticus* (Taq), *Thermus thermophllus* (Tth), *Thermus filiformis*, *Thermis flavus*, *Thermococcus literalis*; and *Pyrococcus furiosus* (Pfu).

When a polymerization reaction is being conducted, it is preferable to provide the components required for such a reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired. All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as the addition of reactants.

Annealing or hybridization in the present method is performed under stringent conditions that allow for specific binding between the primer and the template nucleic acid. Such stringent conditions for annealing will be sequence-dependent and varied depending on environmental parameters.

The amplified MLN 51 cDNA molecules are then analyzed to assess the expression level of the MLN 51 gene. For example, the amplified products are resolved by gel electrophoresis and the bands generated are analyzed to assess the expression level of the MLN 51 gene. When the expression level of the MLN 51 gene from a sample to be diagnosed is measured to be higher than normal samples (or osteoarthritis samples), the sample can be determined to indicate rheumatoid arthritis.

In these instances, where the present method for diagnosing rheumatoid arthritis is carried out by amplification, it comprises the steps of (i) amplifying a nucleic acid sample by use of a primer having a nucleotide sequence complementary to the nucleotide sequence of the MLN 51 gene as set forth in SEQ ID NO:1; and (ii) analyzing the amplified products to determine the expression level of the MLN 51 gene.

The diagnostic kit for rheumatoid arthritis may be constructed by incorporating an antibody that specifically binds to the MLN 51 protein as set forth in SEQ ID NO:2.

The antibody against the MLN 51 protein used in this invention may polyclonal or monoclonal, preferably monoclonal. The antibody can be prepared according to conventional techniques such as a fusion method (Kohler and Milstein, European Journal of Immunology, 6:511-519 (1976)), a recombinant DNA method or a phage antibody library (Clackson et al, Nature, 352:624-628 (1991) and Marks et al, J. Mol. Biol., 222:58, 1-597 (1991)). General procedures for antibody production are described in Harlow, E. and Lane, D., Antibodies: A Laboratory Manual, Cold Spring Harbor Press, New York, 1988; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, N.Y., 1991, which are incorporated herein by reference. For example, the preparation of hybridoma cell lines for monoclonal antibody production is done by fusion of an immortal cell line and antibody producing lymphocytes. This can be done by techniques well known in the art. Polyclonal antibodies may be prepared by injection of the MLN 51 protein antigen into a suitable animal, collecting antiserum containing antibodies from the animal, and isolating specific antibodies by any known affinity techniques.

Where the diagnostic method of this invention is performed using antibodies to the MLN 51 protein, it can be carried out according to conventional immunoassay procedures for detecting rheumatoid arthritis.

Such an immunoassay may be executed by quantitative or qualitative immunoassay protocols, including but not limited to radioimmunoassay, radioimmuno-precipitation, enzyme-linked immunosorbent assay (ELISA), capture-ELISA, inhibition or competition assay, sandwich assay, flow cytometry, immunofluorescence assay and immuoaffinity assay. The immunoassay and immunostaining procedures can be found in *Enzyme Immunoassay*, E. T. Maggio, ed., CRC Press, Boca Raton, Fla., 1980; Gaastra, W., Enzyme-linked immunosorbent assay (ELISA), in *Methods in Molecular Biology*, Vol. 1, Walker, J. M. ed., Humana Press, NJ, 1984; and Ed Harlow and David Lane, *Using Antibodies A Laboratory Manual*, Cold Spring Harbor Press, 1999, which are incorporated herein by reference.

For example, according to the radioimmunoassay method, a radioisotope (e.g., $C^{14}$, $I^{125}$, $P^{32}$ and $S^{35}$) labeled antibody may be used to detect the MLN 51 protein.

In addition, according to the ELISA method, an example of the present method may comprise the steps of: (i) coating a surface of solid substrates with cell (e.g., FLS) lysate to be analyzed; (ii) incubating the coated cell lysate with a primary antibody to the MLN 51 protein; (iii) incubating the resultant surface with a secondary antibody conjugated with an enzyme; and (iv) measuring the activity of the enzyme.

The solid substrate useful in this invention includes carbohydrate polymer (e.g., polystyrene and polypropylene), glass, metal and gel, most preferably microtiter plates.

The enzyme conjugated with the secondary antibody is one which catalyzes colorimetric, fluorometric, luminescence or infra-red reactions, e.g., including alkaline phosphatase, β-galactosidase, luciferase, Cytochrome $P_{450}$ and horseradish peroxidase. When using alkaline phosphatase, bromo-chloroindolylphosphate (BCIP), nitro blue tetrazolium (NBT) or ECF may be used as a substrate for color-developing reactions; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine may be used as a substrate; and in the case of using glucose oxidase, t-NBT (nitroblue tetrazolium) or m-PMS (phenzaine methosulfate) may be used as a substrate.

When the present method is performed in accordance with the capture-ELISA method, a specific example of the present method may comprise the steps of: (i) coating a surface of a solid substrate with a capture antibody capable of binding specifically to the MLN 51 protein; (ii) incubating the capturing antibody with a cell sample (e.g., FLS) to be analyzed; (iii) incubating the product of step (ii) with a detecting antibody which is capable of binding specifically to the MLN 51 protein and conjugated with a label generating a detectable signal; and (iv) detecting the signal generated from the label conjugated with the detecting antibody.

The detecting antibody has a label generating a detectable signal. Examples of the label include, but are not limited to, a chemical (e.g., biotin), an enzymatic (e.g., alkaline phosphatase, horseradish peroxidase, β-galactosidase and Cytochrome $P_{450}$), a radioactive (e.g., $C^{14}$, $I^{125}$, $P^{32}$ and $S^{35}$), a fluorescent (e.g., fluorescein), a luminescent, a chemiluminescent and a FRET (fluorescence resonance energy transfer) label. Various labels and methods for labeling antibodies are well known in the art (Ed Harlow and David Lane, *Using Antibodies*, A Laboratory Manual, Cold Spring Harbor Laboratory Press, 1999).

The detection of the signal generated from the label conjugated with the detecting antibody can be carried out by various processes well known in the art. The detection of the signal enables analysis of the MLN 51 protein in a quantitative or qualitative manner. When biotin and luciferase are used as labels, the signal detection may be achieved by use of streptavidin and luciferin, respectively.

The measurement of signal intensities generated from the immunoassay described above is indicative of rheumatoid arthritis. When the signal to the MLN 51 protein in a biosample to be diagnosed is measured to be higher than in normal samples, the biosample can be determined to indicate rheumatoid arthritis.

The kit of the present invention may optionally include other reagents along with primers, probes or antibodies described above. For instance, when the present kit may be used for nucleic acid amplification, it may optionally include the reagents required for performing PCR reactions such as buffers, DNA polymerase (thermostable DNA polymerase obtained from *Thermus aquaticus* (Taq), *Thermus thermophllus* (Tth), *Thermus filiformis*, *Thermis flavus*, *Thermococcus literalis*, and *Pyrococcus furiosus* (Pfu)), DNA polymerase cofactors, and deoxyribonucleotide-5-triphosphates. The kits, typically, are adapted to contain in separate packaging or compartments the constituents afore-described.

The kits for detecting or diagnosing rheumatoid arthritis permit determining the development, aggravation and alleviation of rheumatoid arthritis. In this regard, the term used herein "detecting or diagnosing" with reference to disease means not only the determination of the existence of disease but also the development, aggravation and alleviation of disease.

According to a preferred embodiment, the kits and methods of the present invention are used to detect or diagnose rheumatoid arthritis developed by hyperproliferation of FLS (fibroblast-like synoviocytes).

The present method for detecting rheumatoid arthritis can diagnose conditions of rheumatoid arthritis in a much more effective and accurate manner, and determine rheumatoid arthritis differentially from osteoarthritis.

In another aspect of this invention, there is provided a method for screening a substance for preventing or treating rheumatoid arthritis, which comprises the steps of: (a) contacting a cell containing the MLN 51 (metastatic lymph node 51) gene or protein with the substance to be analyzed; and (b) measuring the expression level of the MLN 51 gene, the amount of the MLN 51 protein or the activity of the MLN 51 protein, wherein if the expression level of the MLN 51 gene, the amount of the MLN 51 protein or the activity of the MLN 51 protein is measured to be down-regulated, the substance has potency to prevent or treat rheumatoid arthritis.

According to the present method, cells containing the MLN 51 gene or protein are first contacted with substances to be analyzed. Preferably, cells containing the MLN 51 gene or protein are rheumatoid arthritis fibroblast-like synoviocytes. The term "substance" used herein in conjunction with the present screening method refers to a material tested in the present method for analyzing the influence on the expression level of the MLN 51 gene, the amount of the MLN 51 protein or the activity of the MLN 51 protein. The substance includes, but is not limited to, chemical substances, nucleotides, anti-sense-RNA, siRNA (small interference RNA) and extracts of natural sources.

Afterwards, the expression level of the MLN 51 gene, the amount of the MLN 51 protein or the activity of the MLN 51 protein in cells is measured. Where the expression level of the MLN 51 gene, the amount of the MLN 51 protein or the activity of the MLN 51 protein is measured to be down-regulated, the substance is determined to be a candidate to prevent or treat rheumatoid arthritis.

The measurement of the expression level of the MLN 51 gene can be carried out by a variety of methods known in the art. For example, RT-PCR (Sambrook et al., *Molecular Cloning. A Laboratory Manual*, 3rd ed. Cold Spring Harbor Press (2001)), Northern blotting (Peter B. Kaufma et al., *Molecular and Cellular Methods in Biology and Medicine*, 102-108, CRC press), hybridization using a cDNA microarray (Sambrook et al., *Molecular Cloning. A Laboratory Manual*, 3rd ed. Cold Spring Harbor Press (2001)) and in situ hybridization (Sambrook et al., *Molecular Cloning. A Laboratory Manual*, 3rd ed. Cold Spring Harbor Press (2001)) may be used.

When the expression level of the MLN 51 gene is analyzed by RT-PCT, total RNA is first isolated from cells treated with a substance to be analyzed and a first cDNA strand is then synthesized using an oligo dT primer and reverse transcriptase. Then, PCR amplifications are performed using the first cDNA strand as a template and a MLN 51-specific primer set which is exemplified in SEQ ID NOs:3 and 4. Finally, the PCR amplified products are resolved by electrophoresis and bands are analyzed for assessing the expression level of the MLN 51 gene.

The amount of the MLN 51 protein is determined by various immunoassays known in the art. For example, radioimmunoassay, radioimmuno-precipitation, enzyme-linked immunosorbent assay (ELISA), capture-ELISA, inhibition or competition assay and sandwich assay are used for analyzing the amount of the MLN 51 protein.

In still another aspect of this invention, there is provided a pharmaceutical composition for preventing or treating rheumatoid arthritis, which comprises a substance to inhibit the expression of the MLN 51 gene or the activity of the MLN 51 protein as an active ingredient.

In a further aspect of this invention, there is provided a method for preventing or treating rheumatoid arthritis, which comprises administering to a subject a substance to inhibit the expression of the MLN 51 (metastatic lymph node 51) gene or the activity of the MLN 51 protein.

In still a further aspect of this invention, there is provided a use of a substance to inhibit the expression of the MLN 51 (metastatic lymph node 51) gene or the activity of the MLN 51 protein for manufacturing a medicament for detecting, preventing, or treating rheumatoid arthritis.

The pharmaceutical composition of this invention may comprise chemical substances, nucleotides, antisense oligonucleotides, siRNA oligonucleotides or extracts of natural sources.

According to a preferred embodiment, the substance to inhibit the expression of the MLN 51 gene is an antisense or siRNA oligonucleotide having a complementary sequence to the nucleotide sequence of SEQ ID NO:1.

The term "antisense oligonucleotide" used herein is intended to refer to nucleic acids, preferably, DNA, RNA or its derivatives, that are complementary to the base sequences of a target mRNA, characterized in that they bind to the target mRNA and interfere with its translation to protein. The antisense oligonucleotide of this invention means DNA or RNA sequences complementary to and binding to MLN 51 mRNA of SEQ ID NO:1, that are able to inhibit translation, translocation, maturation or other biological functions of MLN 51 mRNA. The antisense nucleic acid is 6-100, preferably, 8-60, more preferably, 10-40 nucleotides in length.

The antisense oligonucleotide may comprise at least one modification in its base, sugar or backbone for its higher inhibition efficacy (De Mesmaeker et al., *Curr Opin Struct Biol.*, 5(3):343-55 (1995)). The modified nucleic acid backbone comprises phosphorothioate, phosphotriester, methyl phosphonate, short chain alkyl or cycloalkyl intersugar linkages or short chain heteroatomic or heterocyclic intersugar linkages. The antisense oligonucleotide may also contain one or more substituted sugar moieties. The antisense nucleic acid may include one or more modified bases, for example, hypoxanthine, 6-methyladenine, 5-me pyrimidines (particularly, 5-methylcytosine), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA*, 86:6553 (1989)), cholic acid (Manoharan et al. *Bioorg. Med. Chem. Let.*, 4:1053 (1994)), a thioether, e.g., hexyl-5-tritylthiol (Manoharan et al. *Ann. N.Y. Acad. Sci.*, 660:306 (1992); Manoharan et al. *Bioorg. Med. Chem. Let.*, 3: 2765 (1993)), a thiocholesterol (Oberhauser et al., *Nucl. Acids Res.*, 20:533 (1992)), an aliphatic chain, e.g., dodecandiol or undecyl residues (Saison-Behmoaras et al. *EMBO J.*, 10:111 (1991); Kabanov et al. *FEBS Lett*, 259:327 (1990); Svinarchuk et al. *Biochimie*, 75:49 (1993), a phospholipid, e.g., di-hexadecyl-rac-glycerol or triethylammonium 1,2-di-O-hexadecyl-rac-glycero-3-H-phosphonate (Manoharan et al. Tetrahedron Lett., 36:3651 (1995); Shea et al. *Nucl. Acids Res.*, 18:3777 (1990)), a polyamine or a polyethylene glycol chain (Manoharan et al. *Nucleosides & Nucleotides,* 14:969 (1995)), or adamantane acetic acid (Manoharan et al. *Tetrahedron Lett.*, 36: 3651 (1995)). Oligonucleotides comprising lipophilic moieties, and methods for preparing such oligonucleotides are known in the art, for example, U.S. Pat. Nos. 5,138,045, 5,218,105 and 5,459,255. The modifications described above enhance stability against nuclease degradation and increase affinity of the antisense oligonucleotide toward its target mRNA.

The antisense molecule is conventionally synthesized in vitro and then transmitted to cells. In addition, it is intracellularly produced by transcription from a foreign sequence. In vitro synthesis involves RNA polymerase I. In vivo transcription for preparing antisense RNA uses vector having origin of recognition region (MCS) in opposite orientation. The antisense RNA preferably comprises a translation stop codon for inhibiting translation to a peptide.

According to a preferred embodiment, the antisense oligonucleotide of this invention has a complementary sequence to the nucleotide sequence spanning nucleotides 200-700 of SEQ ID NO:1.

The pharmaceutical composition of this invention comprises as an active ingredient a siRNA oligonucleotide having a complementary sequence to the nucleotide sequence of SEQ ID NO:1.

The term "siRNA" used herein refers to a nucleic acid molecule mediating RNA interference or gene silencing (see WO 00/44895, WO 01/36646, WO 99/32619, WO 01/29058, WO 99/07409 and WO 00/44914). The use of siRNA to inhibit expression of a target gene provides an effective gene knock-down method or gene therapy method. It was first used in plants, insects, *Drosophila melanogaster* and parasites and recently has been used for mammalian cell research.

The siRNA molecule of this invention may consist of a sense RNA strand (having sequence corresponding to MLN 51 mRNA) and an antisense RNA strand (having sequence complementary to MLN 51 mRNA) and form a duplex structure. Alternatively, the siRNA molecule of this invention may have a single strand structure comprising self-complementary sense and antisense strands.

The siRNA of this invention is not restricted to a RNA duplex of which two strands are completely paired and may comprise a non-paired portion such as a mismatched portion with non-complementary bases and a bulge with no opposite bases. The overall length of the siRNA is 10-100 nucleotides, preferably, 15-80 nucleotides, and more preferably, 20-70 nucleotides.

The siRNA may comprise either blunt or cohesive ends so long as it enables silencing of MLN 51 expression due to an RNAi effect. The cohesive end may be prepared in a 3'-end overhanging structure or a 5'-end overhanging structure.

The siRNA may be constructed by inserting a short nucleotide sequence (e.g., about 5-15 nt) between self-complementary sense and antisense strands. The siRNA expressed forms a hairpin structure by intramolecular hybridization, resulting in the formation of a stem-and-loop structure. The stem-and-loop structure is processed in vitro or in vivo to generate an active siRNA molecule mediating RNAi.

According to a preferred embodiment, the siRNA oligonucleotide of this invention has a complementary sequence to the nucleotide sequence spanning nucleotides 200-700 of SEQ ID NO:1. Most preferably, the siRNA oligonucleotide of this invention is a double stranded oligonucleotide having SEQ ID NOs:5 and 6.

The pharmaceutically acceptable carrier contained in the pharmaceutical composition of the present invention, which is commonly used in pharmaceutical formulations includes, but is not limited to, lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A pharmaceutical composition of this invention may be administered orally or parenterally (e.g., intravenous injection, subcutaneous injection, intramuscular injection and local injection).

The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. According to a preferred embodiment of this invention, a daily suitable dosage unit for human host ranges from 0.001-100 mg/kg(body weight).

According to conventional techniques known to those skilled in the art, the pharmaceutical compositions of this invention can be formulated with a pharmaceutical acceptable carrier and/or vehicle as described above, finally providing several forms including a unit dosage form. Non-limiting examples of the formulations include, but are not limited to, a solution, a suspension or an emulsion, an extract, an elixir, a powder, a granule, a tablet, a capsule, emplastra, a liniment, a lotion and an ointment.

In another aspect of this invention, there is provided a rheumatoid arthritis-related biomarker, comprising the MLN 51 (metastatic lymph node 51) gene of SEQ ID NO:1 or the MLN 51 protein of SEQ IN NO:2.

The biomarker of this invention is significantly specific to rheumatoid arthritis, in particular chronic synovitis.

Figure 1A:
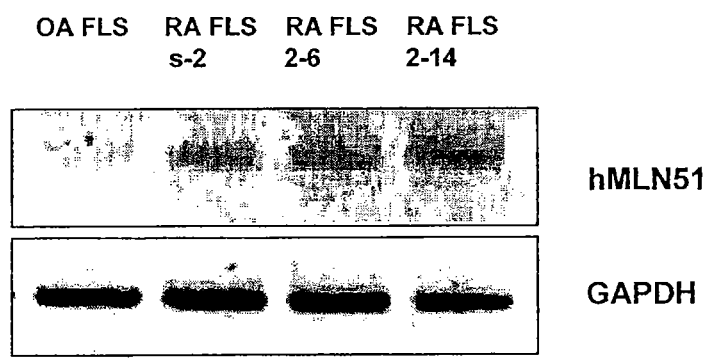
FIG. 1A is a gel photograph showing that the expression level of the MLN51 (metastatic lymph node 51) gene is upregulated in RA-FLS (rheumatoid arthritis fibroblast-like synoviocytes) compared with OA-FLS (osteoarthritis fibroblast-like synoviocytes). Total RNA (1 μg) was extracted from RA FLSs and OA FLS using the TRIZOL reagent. RT-PCR was performed using 5 ng cDNA as template and human MLN51 or GAPDH specific-primers. The results in FIG. 1A are representative of four independent experiments.

The present invention will now be described in further detail by examples. It would be obvious to those skilled in the art that these examples are intended to be more concretely illustrative, and the scope of the present invention as set forth in the appended claims is not limited to or by the examples.

EXAMPLES

Isolation and Culture of RA FLS from RA Patients

FLS cells (RA s-2, 2-6, 2-14, 2-18, 2-36 and 2-38) were prepared from synovectomized tissue of RA patients undergoing joint replacement surgery. Informed consent was obtained from each patient enrolled. The mean age of the patients was 43.8 years, and the disease duration was more than 24 months for all patients. All had erosions visible on radiographs of the hand. All of the RA patients satisfied the diagnostic criteria of American College of Rheumatology (formerly, the American Rheumatism Association) for the classification of RA [13]. RA FLSs were prepared as described previously [14-16]. Briefly, to set up cell lines, synovial tissues were minced into 2-3-mm pieces and treated for 4 hr with 4 mg/ml type 1 collagenase (Worthington Biochemicals, Freehold, N.J., USA) in Dulbecco's modified Eagle's medium (DMEM) at 37° C. in 5% $CO_2$. Dissociated cells were centrifuged at 500 g and were resuspended in DMEM supplemented with 10% FCS, 2 mM L-glutamine, 100 U/ml penicillin, and 100 µg/ml streptomycin. Suspended cells were plated in 75-cm$^2$ culture flasks and cultured at 37° C. in 5% $CO_2$. Medium was replaced every 3 days, and once the primary culture reached confluence, cells were split weekly. Cells at passages 5 to 8 contained a homogeneous population of FLS (<2.5% $CD14^+$, <1% $CD3^+$, and <1% $CD19^+$ in flow cytometry analysis) [14]. Osteoarthritis (OA) FLSs used as the control were prepared from the synovial tissues of three OA patients enrolled. Synovial fluid samples were obtained from the knee joints of different six patients with active RA.

Generation of Different Bone Marrow-Derived Dendritic Cells (BmDCs)

Immature bone marrow-derived dendritic cells (BmDCs) were generated from bone marrow (BM) precursor cells of DBA/1J mice (Japan SLC, Inc.) as described previously [17]. Briefly, bone marrow cells were harvested from femurs and tibias of mice and plated in RPMI-1640 medium supplemented with 10% FBS, 50 µM 2-mercaptoethanol, and high dose (200 U/ml) murine granulocyte macrophage-colony stimulating factor (GM-CSF; Endogen, Inc., Cambridge, Calif.). The medium was changed every other day. Seven days later, non-adherent cells (immature DCs) were harvested by gentle washing with warm PBS. For DC maturation, cells were stimulated for 24 hr with TNF-α (500 U/ml; Endogen, Inc., Cambridge, Calif.) or with LPS (1 µg/ml; Sigma-Aldrich; E. coli, 0127:B8) together with anti-CD40 (clone 3/23 or HM40, 5 µg/ml; BD Pharmingen). The purity and maturation status of DCs were analyzed by a flow cytometer (FACS Calibur; BD Biosciences, San Jose, Calif.) using FITC-conjugated CD44, CD80, CD86, CD205 and MHC II monoclonal antibodies (mAb) or PE-conjugated CD11c, CD40 and ICOSL mAb (BD PharMingen, San Diego, Calif.). Data were analyzed using Cell Quest Software.

BmDC Cell Fine Culture

The BC-1 cells (DC cell line; kindly provided by Dr. Onoe, Division of Immunobiology, Institute for Genetic Medicine, Hokkaido University, Sapporo, Japan), generated from BALB/c mouse spleen [18,19], were cultured and expanded in R1 medium, IMDM containing 10% FCS, 30% NIH/3T3 culture supernatant, and 10 ng/mL mouse recombinant GM-CSF. The BC-1 cells exhibit an immature dendritic cell phenotype.

cDNA Microarray Analysis of RA FLS

We used two kinds of immunologic cDNA microarray chips, HI380 and MI380 (Creagene Inc., Seoul, Korea) for this study. Total RNA was extracted using the TRIZOL reagent (InVitrogen, Carlsbad, Calif.) and purified by using the RNeasy total RNA isolation kit (Qiagen, Valencia, Calif.) according to the manufacturer's instructions. Gene expression profile of human RA-FLS and mouse BmDC were analyzed by using HI380 and MI380 microarray chips, consisting of 384 human and mouse cDNA clones, respectively. Twenty µg of total RNA was reverse-transcribed in the presence of Cy-3 or Cy-5 conjugated dUTP (Amersham Pharmacia Biotech, Piscataway, N.J.) respectively, using SuperScript II and oligo-(dT) 18 primer (InVitrogen, Carlsbad, Calif.) in a reaction volume of 20 µl according to the method suggested by the manufacturer. After the labeling reaction for 1 hr at 42° C., unincorporated florescent nucleotides were cleaned up using a Microcon YM-30 column (Millipore, Bedford, Mass.). The Cy-3 and Cy-5 labeled cDNA probes were mixed together and hybridized to a microarray slide. After overnight at 65° C., the slide was washed twice with 2×SSC containing 0.1% SDS for 5 min at 42° C., once with 0.1×SSC containing 0.1% SDS for 10 min at room temperature, and finally with 0.1×SSC for 1 min at room temperature. The slide was dried by centrifugation at 650 rpm for 5 min. Hybridization images on the slide were scanned by Scanarray lite (Packard Bioscience, Boston, Mass.) and analyzed by GenePix Pro3.0 software (Axon Instrument, Union City, Calif.). Three independent experiments were performed and the ratio of Cy-3 and Cy-5 signal intensity was calculated for each spot. These ratios were log 2-transformed and normalized by subtracting the average of log 2 (Cy3/Cy5) values for internal control genes using Excel (Office 2003, Microsoft Corp.) [21]. For each gene, the mean values were then calculated and a difference of two fold was applied to select up- or down-regulated genes in RA/OA FLSs or immature DC/BM progenitors.

Semi-Quantitative RT-PCR of RA FLS

In order to confirm the up- or down-regulation of the selected gene (MLN51) on the microarray analysis and the expression of MLN51 after siRNA transfection, total RNA was extracted from RA FLSs using the TRIZOL reagent (InVitrogen, Carlsbad, Calif.) and purified using the RNeasy total RNA isolation kit (Qiagen, Valencia, Calif.) according to the manufacturer's instructions. One µg of total RNA was mixed with 50 µM oligo(dT)$_{20}$, and 10 mM dNTP mix, heated at 65° C. for 5 min, and placed on ice for at least 1 min. Then 10×RT buffer [25 mM $MgCl_2$, 0.1 M DTT, RNaseOUT™ (40 U/l)] and SuperScript™ III RT (200 U/l) were added, and the mixture was incubated at 42° C. for 1 hr. The reaction was terminated at 75° C. for 5 min and then chilled on ice. PCR was performed using the cDNA as template and certain gene specific-primers. Primers used in this study were: hMLN51 forward, 5'-AAGACACCGAGGACGAGGAATC-3' (SEQ ID NO:4), hMLN51 reverse, 5'-CCTTCCATAGCTTTCGCTGACG-3'(SEQ ID NO:5), product size 600 bp; mMLN51 forward, 5'-TCCCTGCCCTGCCCTGACTTTA-3'(SEQ ID NO:8), mMLN51 reverse, 5'-CCTCGCGTGCTGTGGGAACTCT-3'(SEQ ID NO:9), product size 800 bp and GAPDH forward, 5'-CCACAGTCCATGCCATCAC-3'(SEQ ID NO:10), GAPDH reverse, 5'-TCCACCACCCTGTTGCTGTA-3'(SEQ ID NO:11), product size 500 bp. The initial cDNA content in each sample was normalized with the amount of glyceraldehyde-3-phosphate dehydrogenase (GAPDH). Amplification reactions were performed in a 20 μl volume using 5 ng or 10 ng of each cDNA in a Perkin-Elmer DNA thermocycler 9600 Prism for 35 cycles. The PCR reactions were separated on 1.2% agarose gels and stained with ethidium bromide.

Measurement of Cytokines and GM-CSF Levels in RA Synovial Fluids (SFs)

IL-1β and TNF-α were measured in the SFs using the Human Cytometric Bead Array (CBA) (BD Pharmingen, San Diego, Calif.), and GM-CSF using the Human ELISA kits (Endogen, Inc., Cambridge, Mass.) following the manufacturer's instructions.

Western Blot Analysis

RA FLS samples were lysed in boiled buffer containing 1% SDS. Each sample, containing a normalized amount of total protein (about 30 μg of protein), was separated by 10% SDS-PAGE and transferred to a nitrocellulose membrane. This was then immersed in blocking buffer (5% skimmed milk and 0.1% Tween 20 in PBS, pH 7.4) for 1 hr at room temperature and incubated with anti-hMLN51 rabbit serum (1:1,000 dilution) and anti-GAPDH (1:5,000 dilution) or anti-α-tubulin (1:5,000 dilution) in blocking buffer overnight at 4° C. Anti-hMLN51 serum was obtained from rabbits immunized with recombinant hMLN51 protein. After the incubation, the membrane was probed with horseradish peroxidase-labeled anti-rabbit IgG antibody (1:5,000 dilution) in PBS (containing of 0.05% Tween 20 and 5% skimmed milk powder) for 30 minutes at room temperature. The proteins in the membrane were detected by enhanced chemiluminescence (Amersham, Little Chalfont, Bucks., UK) and bands were detected by autoradiography with X-ray film (Fujifilm).

Treatment of RA FLS with SF, Cytokine or Neutralizing Antibodies

RA FLSs were cultured in 12-well plates in high glucose DMEM supplemented with 10% FBS, penicillin, streptomycin, and glutamine at 37° C. in a 5% $CO_2$ humidified incubator. In the case of SF and cytokines-treatment, RA FLSs were treated with SFs to recover their growth as follows: 1/100, 1/50, or 1/10 dilution in culture media. Human Inflammatory cytokines (IL-1β and TNF-α, 100 ng/ml of each) and growth factor (GM-CSF, 10 or 100 ng/ml) were obtained from Pepro Tech, Rocky Hill, N.J. or BD Pharmingen, San Diego, Calif. Monoclonal neutralizing antibodies to GM-CSF (BVD2-23B6, IgG2a, 300 ng/ml), IL-1β (AS10, IgG1, 500 ng/ml) and TNF-α (MAb1, IgG1, 2 μg/ml) were purchased from BD Pharmingen, San Diego, Calif. During the experiments, the trypan blue exclusion method was employed for the evaluation for cell proliferation.

siRNA Synthesis and Transfection

The siRNA synthesis was performed using the Silencer™ siRNA Cocktail Kit (RNase III; Ambion Inc., Austin, Tex.). The siRNA sequence was used for targeted silencing of human MLN51 [Genebank access number: NM007359] and mouse MLN51 [Genebank access number: AJ292072]. The oligonucleotides used for the dsRNA synthesis were in hMLN51, 5'-TAATACGACTCACTATAGGGTACTCGTAAGATGGCGGACCGG (SEQ ID NO:6) and 5'-TAATACGACTCACTATAGGGTCCGTCCCCACTTTGCCTC (SEQ ID NO:7), and in mMLN51, 5'-TAATACGACTCACTATAGGGTACTCGTAAGATGGCGGACCGG-3'(SEQ ID NO:6) and 5'-TAATACGACTCACTATAGGGTACTCTGCCTCTCCCCAGTCAC-3'(SEQ ID NO:12). The siRNA sequences were selected in size ranging from 228 to 686 bp, as described previously [20,21]. The siRNA synthesis was performed according to the manufacturer's protocol. Non-silencing or negative control siRNA (Silencer™ Negative Control #2 siRNA; Ambion Inc.) is an irrelevant siRNA with random nucleotides and no known specificity. Ten thousand RA FLS per well were seeded in 24-well plates in DMEM supplemented with 10% FBS. The cells were transfected with the siRNA on the next day using GenePORTER 2 Transfection Reagent™ (Gene Therapy Systems, San Diego, Calif.) according to the manufacturer's protocol. After 24 hr post-transfection, the media was added with the fresh DMEM supplemented with 10% FBS. Everyday the cells were harvested, and then counted. Total RNA extracted from the transfected cells was used to perform semi-quantitative RT-PCR.

Statistical Analysis

The results are expressed as the mean±SEM. The Mann-Whitney U test was used for all statistical analysis. A p value of less than 0.05 was considered significant.

Results

RA is a heterogeneous autoimmune disease. However, these heterogeneous chronic diseases are recently able to be monitored in line with their gene expression patterns by microarray in molecular studies [24]. Histologically, RA joints are characterized by chronic inflammation with hyperplasia in the synovial lining cells. It is now well established that FLS actively participate in RA synovitis. FLS in RA joints aggressively proliferate to form a pannus, which eventually destroys articular bone and cartilage [25,26]. A number of growth factors or cytokines have been described in association with the proliferative response of FLS, such as TGF-β, PDGF, fibroblast growth factor, IL-1β, TNF-α, and IL-6. However, in trials of those therapeutic agents, response was not achieved in a significant proportion of patients, suggesting that some other important factors still remain undiscovered.

To our knowledge the present invention is the first demonstration of the ability of the MLN51 gene to be essential for tumorigenicity of RA FLS in vitro under investigation by siRNA gene knock-down experiments. Our results show that the SF-mediated growth of RA FLS was markedly blocked by anti-GM-CSF neutralizing antibody, and additionally growth-retarded RA-FLS recovered their proliferation capacity by adding GM-CSF into the culture. These results imply that GM-CSF in SF plays an important role for the hyperproliferation of RA FLS. Moreover, in the microarray analysis and semi-quantitative RT-PCR, we found that the MLN51 gene was highly expressed in the hyperactive RA FLS in low passage or RA FLS cultured in the presence of SF. MLN51 knock-down by siRNA completely blocked the GM-CSF/SF-mediated hyperproliferation of RA FLS, suggesting that the MLN51 is strongly involved in the chronic synovitis in RA patients.

Firstly, we extracted total RNA from RA FLSs and one OA FLS as a control, which were labeled and hybridized to HI380 micrarrays containing 384 gene clones. Differential hybridization was performed with Cy-5-labeled RA cDNA and Cy-3-labeled OA cDNA probes. Through the microarray analysis, we found that MLN51, a novel gene in association with RA, was markedly upregulated among the many upregulated genes selected on the basis of their immunologic characteristics (Table 1).

TABLE 1

The MLN52 gene expression upregulated in RA FLS

| Patient Sample | Intensity of RA FLS | Intensity of OA FLS | Folds of expression |
|---|---|---|---|
| RA FLS s-2 | 12347 | 4429 | 2.78776 |
| RA FLS 2-6 | 15621 | 8210 | 1.90267 |
| RA FLS 2-14 | 22193 | 11239 | 1.97464 |

Figure 1B:
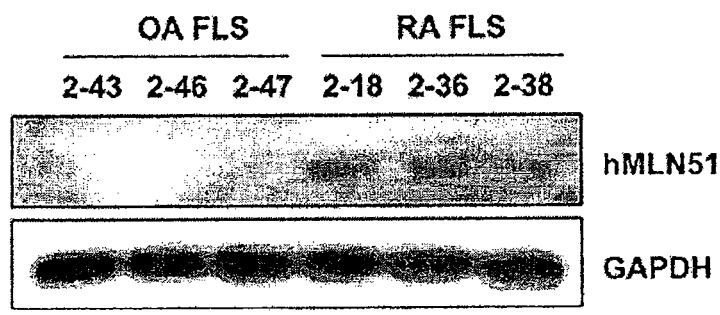
FIG. 1B shows results of Western blot analysis of MLN51 in FLS samples. RA FLSs (2-18, 2-36 and 2-38) and OA FLSs (2-43, 2-46 and 2-47) isolated from each patient were seeded at $5 \times 10^4$ cells per well in a six-well plate. FLSs grown in high-glucose DMEM supplemented with 10% FBS were harvested, separated by 10% SDS-PAGE, transferred to a nitrocellulose membrane and then probed with anti-hMLN51 rabbit serum (1:1,000 dilution) and horseradish peroxidase-conjugated anti-rabbit IgG (1:5,000 dilution). The results in FIG. 1A are representative of four independent experiments.

We next performed semi-quantitative RT-PCR with the MLN51 gene selected in the analysis to confirm the differences observed in cDNA microarray analysis. MLN51 overexpression in RA FLSs was confirmed by RT-PCR analysis with three different RA FLS samples (FIG. 1a) and by Western blot experiments with three additional different RA FLS samples (FIG. 1b).

Figure 2A:
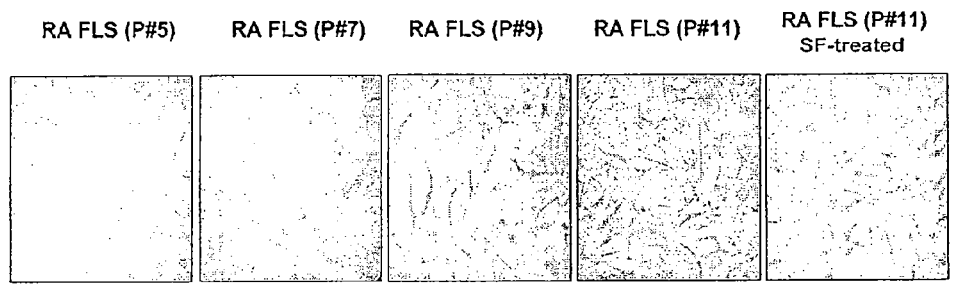
FIG. 2 represents (A) the difference in morphology and (B) the growth kinetics of RA FLS on passage No. 5, No. 7, No. 9, or No. 11 and SF(synovial fluid)-treated No. 11. RA FLSs were used on passage No. 5, 7, 9, and 11 to observe the morphologies of different RA FLSs. RA FLSs were treated with SFs (1/50 dilution) to recover their growth with 1/50 dilution in culture media. The culture was incubated for 2 days. Moreover, RA FLSs were used on passage No. 3, 5, and 11 to measure their growth kinetics. The high passage No. RA FLS were treated with SFs to recover their growth as follows: 1/100, 1/50, or 1/10 dilution in culture media. The culture was incubated for 6 days. The treated SF volume is as follows: (panel A) 1/10 dilution; (panel B) 1/100, 1/50, and 1/10 dilution of the high passage No. RA FLS culture media. SD (n=3). *, P<0.01.
FIG. 2C represents the concentrations of GM-CSF and cytokines in SF from different RA patients. A total of six SFs were analyzed using human GM-CSF and cytokines concentration using ELISA kit (Pierce Endogen, Inc.) and CBA kit (BD Biosciences, Inc.) according to the manufacturer's instruction.
FIG. 2D is a gel photograph showing that MLN51 expression is upregulated in SF or GM-CSF-treated RA FLS compared with untreated RA FLS. Total RNA (1 μg) was extracted from the conditioned cells using the TRIZOL reagent. RT-PCR was performed using 5 ng cDNA as template and human MLN51 or GAPDH specific-primers. The high passage No. RA FLSs were treated with GM-CSF (100 ng/ml) or SF, 1/10 volume of the culture media at every 2 days for 6 days.
Figure 2B:
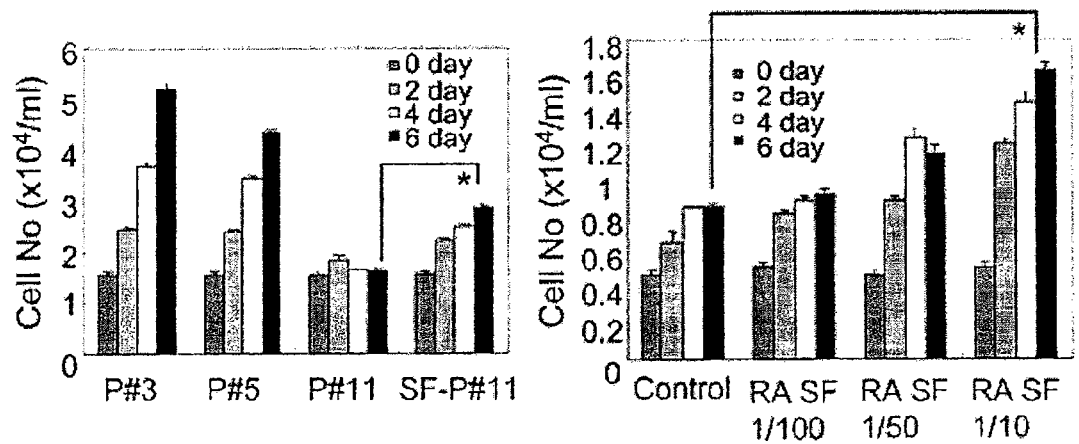
Figure 2C:
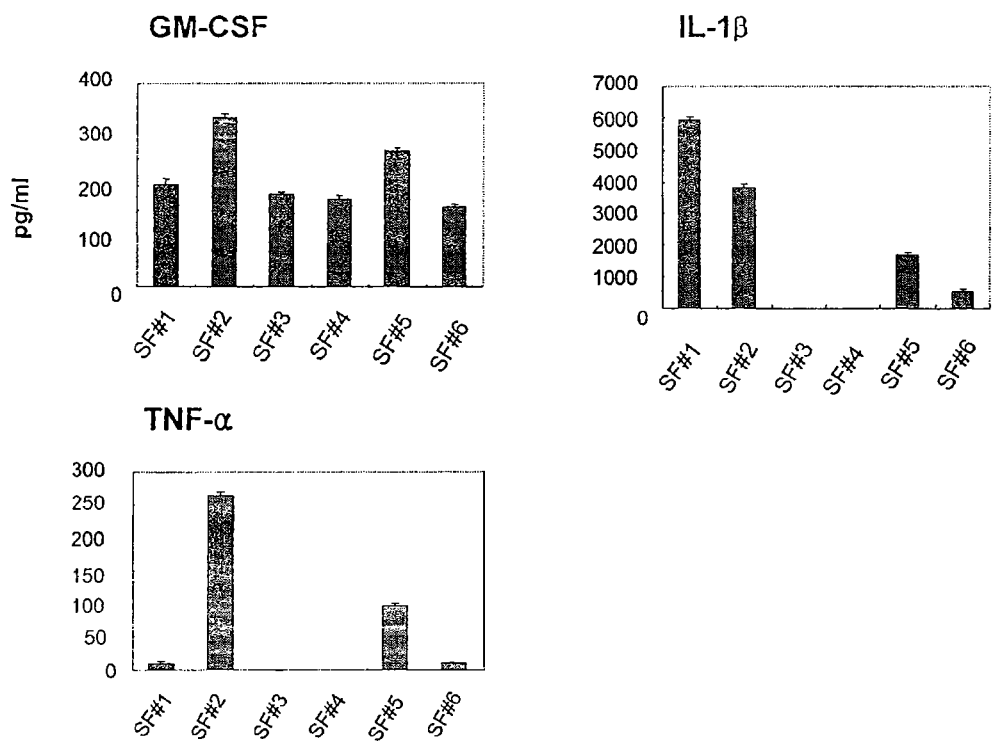
Figure 2D:

We next investigated whether SFs have an effect on recovery of the reduced growth of high passage No. RA FLS or not, which one of factors in SFs have a growth-recovering effect and whether the recovering factor plays a role in the expression of MLN51 or not. First of all, we observed the morphology of RA FLS (RA 2-14) on the different passage with the inverted microscope. As shown in FIG. 2A, the morphologies of RA FLS changed with the passage number. A high passage No. RA FLS (passage No. 11) had many dendrites and showed widely reduced growth rate. However, the SF-treatment (SF No. 2) on RA FLS culture (right end panel of FIG. 2A) changed the morphology of high passage No. 11 into the morphology of approximately passage No. 7-9. In addition, we performed measurement of the growth kinetics of different passage number and SF-treated RA FLSs. The SF-treatment (SF No. 2) on RA FLS culture (RA 2-14) recovered the growth rate of the high passage No. RA FLS (FIG. 2B, Left panel). The high passage No. RA FLS remarkably recovered from growth retardation when cultured in the presence of 1/10-diluted SF (FIG. 2B, Right panel). We next quantified inflammatory cytokine levels in SFs (FIG. 2C). These results demonstrated that GM-CSF in all SFs from six RA patients evenly exists to a significant level, as compared to other inflammatory cytokines, IL-1β and TNF-α. Moreover, the expression patterns of hMLN51 gene upregulated by SF (SF No. 2) and GM-CSF were confirmed to infer a function of hMLN51 in proliferation of SF-treated or GM-CSF-treated RA FLS (RA 2-14) (FIG. 2D). These results suggested that the increased hMLN51 in RA FLS treated with SF or GM-CSF may positively function on cell proliferation.

Figure 3A:
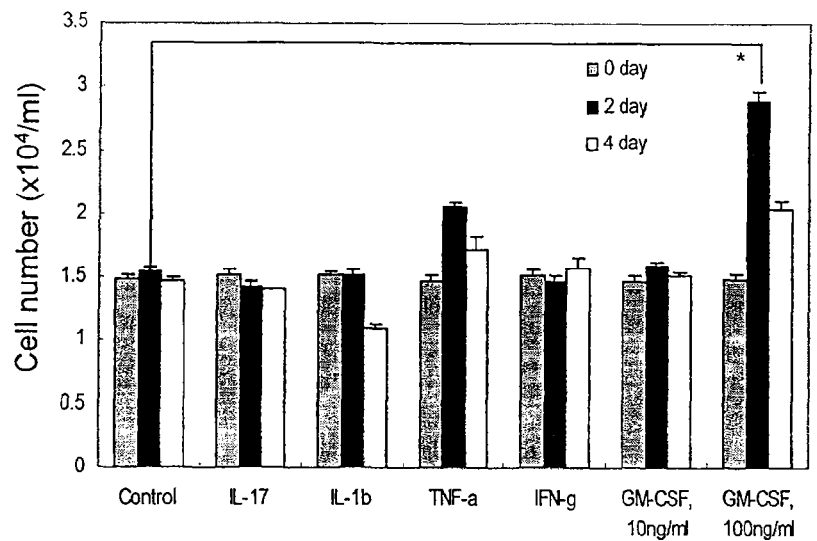
FIG. 3A is a graph demonstrating effects of GM-CSF and cytokines on the growth of high passage No. RA FLS. RA FLS were seeded at $1.5 \times 10^4$ cells/well in triplicate in a 24-well plate. Cells were cultured in high DMEM supplemented with 10% FBS, and supplemented with 100 ng/ml cytokines and 10 or 100 ng/ml GM-CSF at day 0.
Figure 3B:
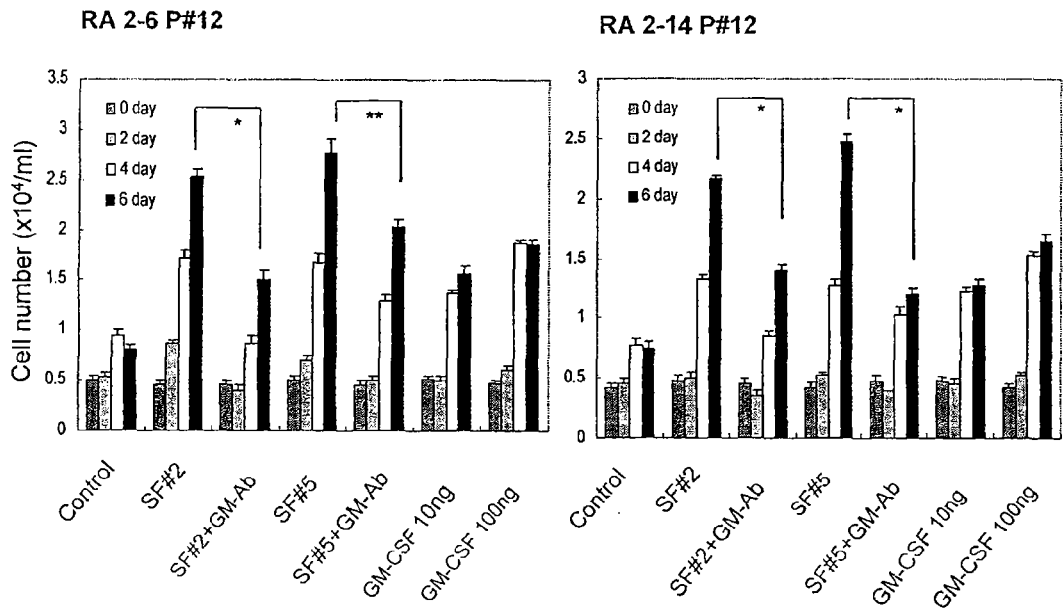
FIG. 3B is a graph demonstrating the suppression of proliferation of SF-treated RA FLS by anti-GM-CSF. The high passage No. RA FLSs were cultured at a concentration of $0.5 \times 10^4$/well in a 24-well plate in high DMEM supplemented with 10% FBS alone or high DMEM supplemented with 10% FBS containing GM-CSF (10 or 100 ng/ml), SF, 1/10 volume of the culture media or SF and anti-GM-CSF (300 ng/ml). The cytokine and SF were added every two days in the presence or absence of mAb. Cells were counted and assessed for viability by trypan blue at every 2 days. Bars, SD (n=3). *, P<0.01. **, P<0.05.

It has been reported that there are many kinds of cytokines and growth factors in RA microenvironments. To identify factors having an effect on the growth of RA FLS, we investigated the effects of the inflammatory cytokines or growth factors on the growth of RA FLS (2-14) in vitro. The results show that GM-CSF and TNF-α may have an effect on recovering the growth of high passage No. RA FLS (FIG. 3A). Our present results are supported by the fact that resident joint cells (chondrocytes and synovial fibroblasts) produce GM-CSF in culture in response to TNF-α and IL-1β [27, 28]. In order to address the effects of GM-CSF in SF on the growth of RA FLS, we cultured the RA FLS in culture media containing SF and anti-GM-CSF monoclonal antibody (mAb) or recombinant GM-CSF. Incubation of two different RA FLSs with SFs containing anti-GM-CSF mAb impaired the SF-mediated FLS proliferation efficacy (FIG. 3B) to a significant level. These results imply that GM-CSF in SF plays an important role for the hyperproliferation of RA FLS. Viability was 98-99% in all cultures (data not shown). Growth-retarded RA FLS significantly recovered their proliferation capacity by GM-CSF in a dose-dependent manner.

Figure 4:
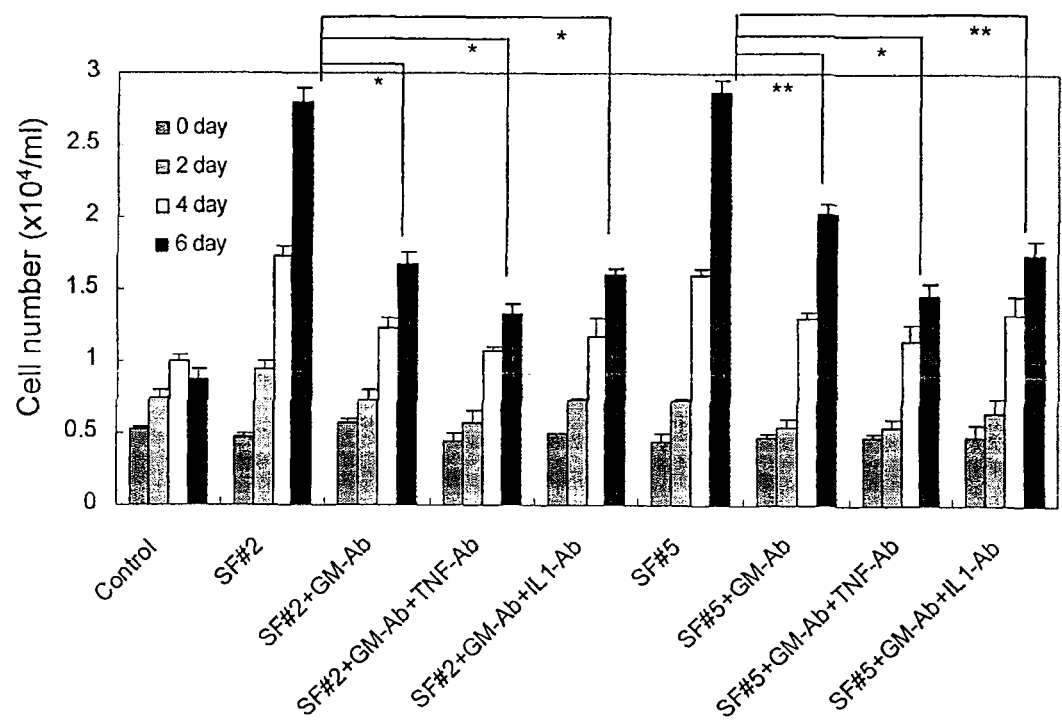
FIG. 4 is a graph representing the inhibition of proliferation of SF-treated RA FLS by anti-GM-CSF and anti-TNF-α. The high passage No. RA FLSs were cultured at a concentration of $0.5 \times 10^4$/well in a 24-well plate in high DMEM supplemented with 10% FBS alone or high DMEM supplemented with 10% FBS containing SF, 1/10 volume of the culture media or SF and anti-GM-CSF (300 ng/ml), anti-IL-1β (500 ng/ml) or anti-TNF-α (2 μg/ml). The cytokine and SF were added every two days in the presence or absence of mAb. Cells were counted and assessed for viability by trypan blue every 2 days. Bars, SD (n=3). *, P<0.01. **, P<0.05.

Moreover, to investigate the effects of IL-1β or TNF-α in SF on recovering the growth of RA FLS, we cultured the RA FLS in SF-containing media in the presence of anti-GM-CSF, anti-GM-CSF+anti-IL-1β or anti-GM-CSF+anti-TNF-α mAbs. As shown in FIG. 4, treatment with both anti-GM-CSF and anti-TNF-α mAbs showed a little more suppression than those shown in treatment with anti-GM-CSF mAb alone, on the SF-mediated proliferation. Our results shown in FIG. 3B and FIG. 4 suggest that not only GM-CSF but also some other proinflammatory cytokines like TNF-α are likely involved in the growth rate of RA FLS. However, anti-IL-1β mAb did not show any clear effects on the SF-mediated proliferation of RA FLS, suggesting that unexpectedly IL-1β in SF would not be directly involved in the FLS hyperproliferation in RA pathogenesis. These cytokine effects on the FLS proliferation were repeated in the tendency of hMLN51 gene expression level.

Figure 5A:
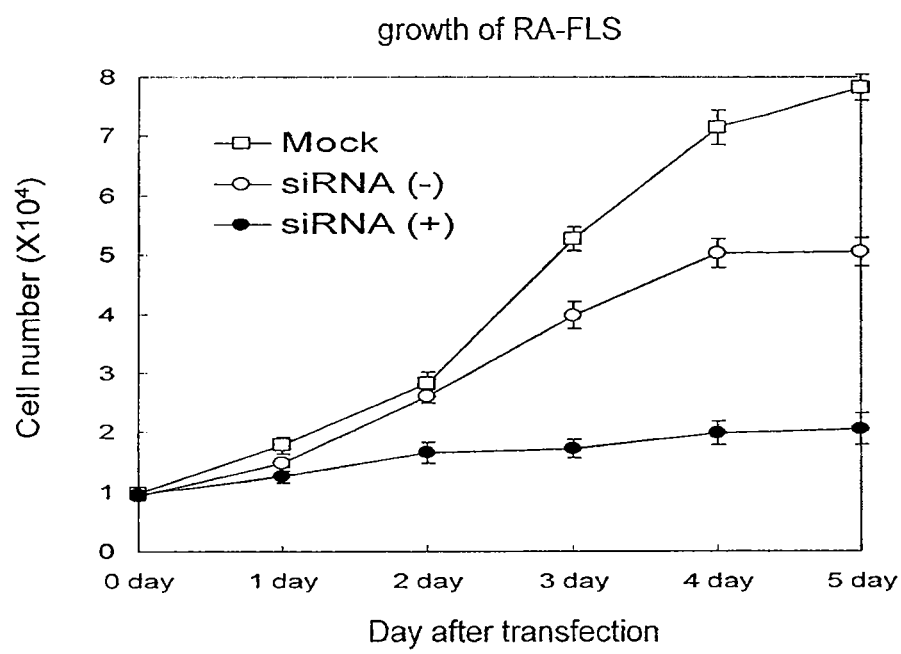
FIGS. 5A and 5B represent effects of siRNA of the human MLN51 gene on the growth of RA FLS cells. Cells ($1 \times 10^4$) were transfected with 4 μg siRNA-hMLN51 genes, negative control siRNA or Geneporter alone (mock transfected). The transfected cells were cultured in the growth media from day 0 to day 5 and counted every day. The trypan blue exclusion method was employed for the evaluation of cell proliferation (FIG. 5A). Total RNA from the treated RA FLS was extracted using the Trizol method. RT-PCR was performed to assess expression of the hMLN51 gene and GAPDH using the primers (FIG. 5B).

On the other hand, to examine the specific requirement for the hMLN51 gene in cell proliferation, siRNA prepared from the 5' region of human MLN51 cDNA was introduced into passage No. 5 RA FLS. The growth kinetics of the transfected RA FLS was monitored for 5 days, and the level of the corresponding hMLN51 mRNA was measured by semi-quantitative RT-PCR. We observed that the treatment of FLS with hMLN51-siRNA causes a complete abrogation of RA FLS proliferation (FIG. 5A). At this time, it was observed that the transfected RA FLS had suppressed expression of the hMLN51 gene for five days. These results suggest that the MLN51 gene plays a crucial role for the hyperproliferation of RA FLS.

Figure 5B:
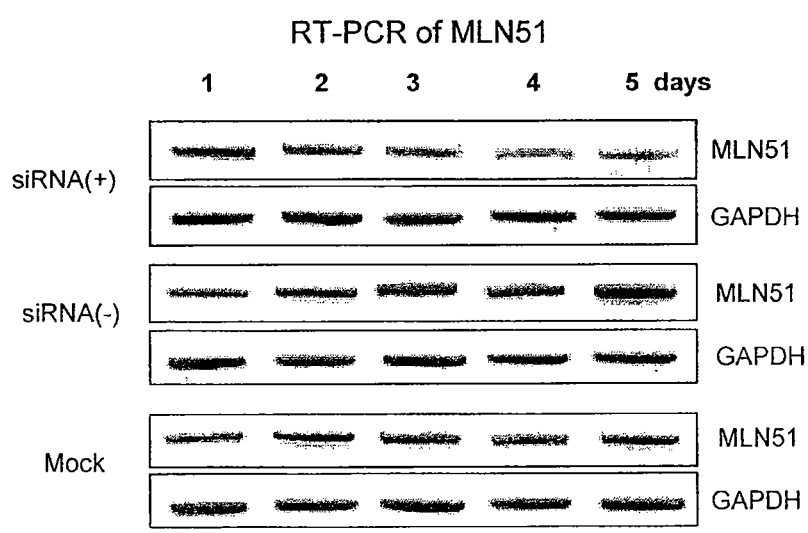
Figure 6A:
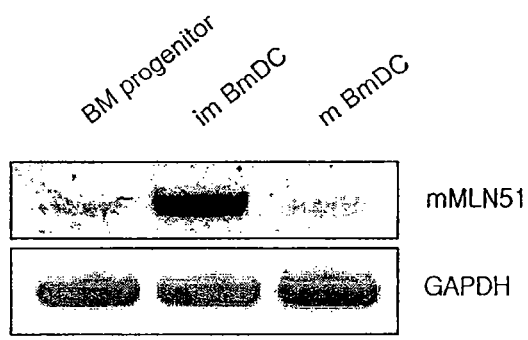
FIG. 6A is a gel photograph showing that MLN51 expression is upregulated in immature BmDCs compared with BM cells and mature BmDCs. Total RNA (1 μg) was extracted from the cells using the TRIZOL reagent. RT-PCR was performed using 5 ng cDNA as template and mouse MLN51 or GAPDH specific-primers.
Figure 6B:
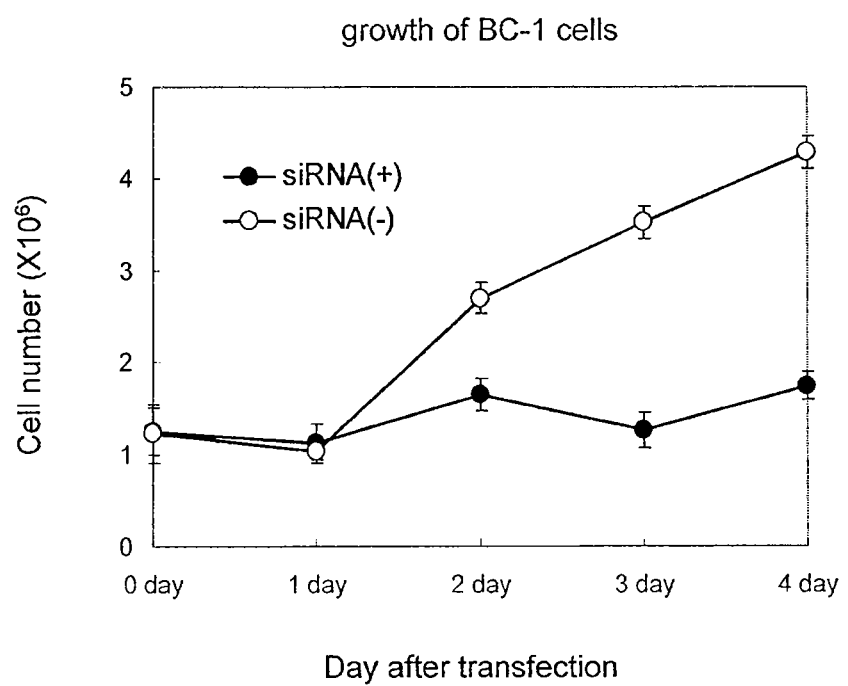
FIG. 6B is a graph demonstrating effects of siRNA of MLN51 gene on the growth of BC-1 cells.
Figure 6C:
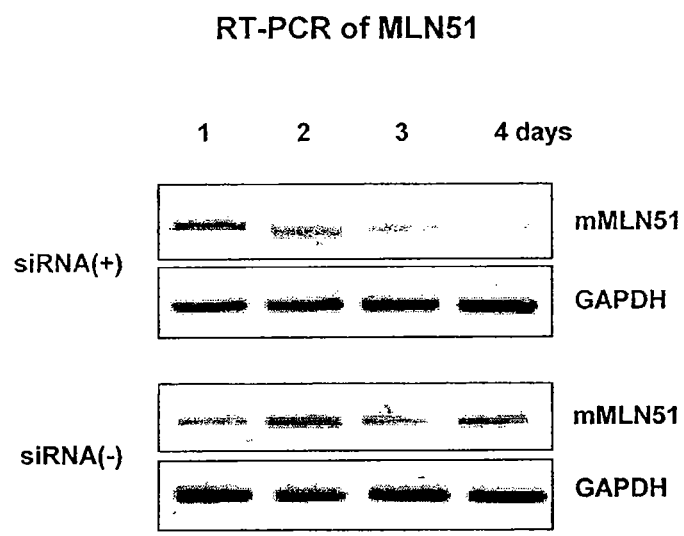
FIG. 6C represents the results of semi-quantitative RT PCR to assess expression of the hMLN51 gene in BC-1 cells incubated with siRNA-mMLN51. The cells ($1\times10^6$) were transfected with 4 µg siRNA-mMLN51 genes or Geneporter alone (mock transfected). RNA from the transfected BC-1 cells was extracted using the Trizol method. RT-PCR was performed to assess expression of the mMLN51 gene and GAPDH using the primers.

We next generated BmDCs from DBA/1J mice, which are frequently used as an arthritis model. It is known that the DBA/1 mouse strain having a H-2q haplotype readily develops arthritis after immunization with heterologous or autologous type II collagen, including rat, bovine or chick CII [29]. Also, DCs are particularly relevant in the pathogenesis of most inflammatory arthopathies because of their potent Ag-presenting activity and unique ability to activate naïve T cells [30-32]. In addition, DC populations have been described in the synovial membrane in RA, although their functional contribution to disease remains difficult to assess [33-35]. Immature BmDCs were generated from BM progenitors by culturing progenitors in the presence of GM-CSF alone. Immature BmDCs were matured with LPS and anti-CD40, and we then performed semi-quantitative RT-PCR of MLN51 gene expression to confirm the differences observed in cDNA microarray analysis. As shown in FIG. 6A, MLN51 was highly expressed only in immature BmDCs while it was barely detected in BM progenitor or mature BmDC, implying that GM-CSF treatment is quite associated with MLN51 expression. We hypothesized that MLN51 may have some important roles in immature dendritic cells in line with their specific biological functions or some viability. We investigated a function of MLN51 on the growth of dendritic cells using the immature DC cell line, BC-1 cells. We established a protocol for MLN51 siRNA transfection using an siRNA Cocktail Kit to evaluate the toxicity of the transfection reagent on the viability of BC-1 cells. BC-1 cells transfected with MLN51 siRNA every other day, were harvested everyday to measure the cell proliferation and MLN51 mRNA expression by RT-PCR. As shown in RA-FLS (FIG. 5), MLN51 knock-down by MLN51-specific siRNA (FIG. 6C) abrogated the proliferation of BC-1 cells (FIG. 6B). This means that MLN51 play an important role for the proliferation of not only FLS but also established DC cell lines.

Taken together, our results strongly suggest that MLN51 whose expression is depending on the GM-CSF signaling, may have a critical role in the hyperproliferation of FLS in RA pathogenesis.

The present invention provides a kit for detecting rheumatoid arthritis, a method for screening a substance for preventing or treating rheumatoid arthritis, a pharmaceutical composition for preventing or treating rheumatoid arthritis and a rheumatoid arthritis-related biomarker. The MLN 51 gene and protein are closely related to the development of rheumatoid arthritis and serve as biomarker and therapeutic target for rheumatoid arthritis, particularly chronic synovitis.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1. Hale L, Haynes B: Pathology of rheumatoid arthritis and associated disorders In: *Arthritis and Allied Conditions: A Textbook of Rheumatology*. Edited by Koopman W. Baltimore: Williams and Wilkins; 1997: 993.
2. Okada Y: Proteinases and matrix degradation. In: *Kelly's Textbook of Rheumatology*. Edited by Ruddy S, Harris E D, Sledge J C B, vol. 1. Philadelphia: WB Saunders; 2001: 55.
3. Mountz J D, Wu J, Cheng J, Zhou T: Autoimmune disease. A problem of defective apoptosis. *Arthritis Rheum* 1994, 37(10):1415-1420.
4. Firestein G S, Nguyen K, Aupperle K R, Yeo M, Boyle D L, Zvaifler N J: Apoptosis in rheumatoid arthritis: p53 overexpression in rheumatoid arthritis synovium. *Am J Pathol* 1996, 149(6):2143-2151.
5. Nishioka K, Hasunuma T, Kato T, Sumida T, Kobata T: Apoptosis in rheumatoid arthritis: a novel pathway in the regulation of synovial tissue. *Arthritis Rheum* 1998, 41(1): 1-9.
6. Nakajima T, Aono H, Hasunuma T, Yamamoto K, Shirai T, Hirohata K, Nishioka K: Apoptosis and functional Fas antigen in rheumatoid arthritis synoviocytes. *Arthritis Rheum* 1995, 38(4):485-491.
7. Firestein G S, Yeo M, Zvaifler N J: Apoptosis in rheumatoid arthritis synovium. *J Clin Invest* 1995, 96(3):1631-1638.
8. Degot S, Regnier C H, Wendling C, Chenard M P, Rio M C, Tomasetto C: Metastatic Lymph Node 51, a novel nucleocytoplasmic protein overexpressed in breast cancer. *Oncogene* 2002, 21(28):4422-4434.
9. Degot S, Le Hir H, Alpy F, Kedinger V, Stoll I, Wendling C, Seraphin B, Rio M C, Tomasetto C: Association of the breast cancer protein MLN51 with the exon junction complex via its speckle localizer and RNA binding module. *J Biol Chem* 2004, 279(32):33702-33715.
10. Ballut L, Marchadier B, Baguet A, Tomasetto C, Seraphin B, Le Hir H: The exon junction core complex is locked onto RNA by inhibition of eIF4AIII ATPase activity. *Nat Struct Mol Biol* 2005, 12(10):861-869.
11. Shibuya T, Tange T O, Stroupe M E, Moore M J: Mutational analysis of human eIF4AIII identifies regions necessary for exon junction complex formation and nonsense-mediated mRNA decay. *Rna* 2006, 12(3):360-374.
12. Tange T O, Shibuya T, Jurica M S, Moore M J: Biochemical analysis of the DC reveals two new factors and a stable tetrameric protein core. *Rna* 2005, 11(12):1869-1883.
13. Arnett F C, Edworthy S M, Bloch D A, McShane D J, Fries J F, Cooper N S, Healey L A, Kaplan S R, Liang M H, Luthra H S et al. The American Rheumatism Association 1987 revised criteria for the classification of rheumatoid arthritis. *Arthritis Rheum* 1988, 31(3):315-324.
14. Yoo S A, Bae D G, Ryoo J W, Kim H R, Park G S, Cho C S, Chae C B, Kim W U: Arginine-rich anti-vascular endothelial growth factor (anti-VEGF) hexapeptide inhibits collagen-induced arthritis and VEGF-stimulated productions of TNF-alpha and IL-6 by human monocytes. *J Immunol* 2005, 174(9):5846-5855.
15. Hwang S Y, Kim J Y, Kim K W, Park M K, Moon Y, Kim W U, Kim H Y: IL-17 induces production of IL-6 and IL-8 in rheumatoid arthritis synovial fibroblasts via NF-kappaB- and PI3-kinase/Akt-dependent pathways. *Arthritis Res Ther* 2004, 6(2):R120-128.
16. Min S Y, Hwang S Y, Jung Y O, Jeong 3, Park S H, Cho C S, Kim H Y, Kim W U: Increase of cyclooxygenase-2 expression by interleukin 15 in rheumatoid synoviocytes. *J Rheumatol* 2004, 31(5):875-883.
17. Lutz M B, Kukutsch N, Ogilvie A L, Rossner S, Koch F, Romani N, Schuler G: An advanced culture method for generating large quantities of highly pure dendritic cells from mouse bone marrow. *J Immunol Methods* 1999, 223 (1):77-92.
18. Yanagawa Y, Iijima N, Iwabuchi K, Onoe K: Activation of extracellular signal-related kinase by TNF-alpha controls the maturation and function of murine dendritic cells. *J Leukoc Biol* 2002, 71(1):125-132.
19. Winzler C, Rovere P, Rescigno M, Granucci F, Penna G, Adorini L, Zimmermann V S, Davoust J, Ricciardi-Castagnoli P: Maturation stages of mouse dendritic cells in growth factor-dependent long-term cultures. *J Exp Med* 1997, 185(2):317-328.
20. Ahn J H, Lee Y, Jeon C, Lee Si, Lee B H, Choi K D, Bae Y S: Identification of the genes differentially expressed in human dendritic cell subsets by cDNA subtraction and microarray analysis. *Blood* 2002, 100(5):1742-1754.
21. Yang Y H, Dudoit S, Luu P, Lin D M, Peng V, Ngai J, Speed T P: Normalization for cDNA microarray data: a robust composite method addressing single and multiple slide systematic variation. *Nucleic Acids Res* 2002, 30(4): e15.
22. Yang D, Buchholz F, Huang Z, Goga A, Chen C Y, Brodsky F M, Bishop J M: Short RNA duplexes produced by hydrolysis with *Escherichia coli* RNase III mediate effective RNA interference in mammalian cells. *Proc Natl Acad Sci USA* 2002, 99(15):9942-9947.
23. Calegari F, Haubensak W, Yang D, Huttner W B, Buchholz F: Tissue-specific RNA interference in postimplantation mouse embryos with endoribonuclease-prepared short interfering RNA. *Proc Natl Acad Sci USA* 2002, 99(22): 14236-14240.
24. Oertelt S, Selmi C, Invernizzi P, Podda M, Gershwin M E: Genes and goals: an approach to microarray analysis in autoimmunity. *Autoimmun Rev* 2005, 4(7):414-422.
25. Pap T, Muller-Ladner U, Gay R E, Gay S: Fibroblast biology. Role of synovial fibroblasts in the pathogenesis of rheumatoid arthritis. *Arthritis Res* 2000, 2(5):361-367.
26. Yamanishi Y, Firestein G S: Pathogenesis of rheumatoid arthritis: the role of synoviocytes. *Rheum Dis Clin North Am* 2001, 27(2):355-371.
27. Campbell I K, Bendele A, Smith D A, Hamilton J A: Granulocyte-macrophage colony stimulating factor exacerbates collagen induced arthritis in mice. *Ann Rheum Dis* 1997, 56(6):364-368.

28. Hamilton J A: GM-CSF in inflammation and autoimmunity. *Trends Immunol* 2002, 23(8):403-408.
29. Holmdahl R, Jansson L, Andersson M, Larsson E: Immunogenetics of type II collagen autoimmunity and susceptibility to collagen arthritis. *Immunology* 1988, 65(2):305-310.
30. Banchereau J, Steinman R M: Dendritic cells and the control of immunity. *Nature* 1998, 392(6673):245-252.
31. Mellman I, Turley S J, Steinman R M: Antigen processing for amateurs and professionals. *Trends Cell Biol* 1998, 8(6):231-237.
32. Steinman R M: DC-SIGN: a guide to some mysteries of dendritic cells. *Cell* 2000, 100(5):491-494.
33. Thomas R, Davis L S, Lipsky P E: Rheumatoid synovium is enriched in mature antigen-presenting dendritic cells. *J Immunol* 1994, 152(5):2613-2623.
34. Summers K L, O'Donnell J L, Williams L A, Hart D N: Expression and function of CD80 and CD86 costimulator molecules on synovial dendritic cells in chronic arthritis. *Arthritis Rheum* 1996, 39(8):1287-1291.
35. Pettit A R, Thomas R: Dendritic cells: the driving force behind autoimmunity in rheumatoid arthritis? *Immunol Cell Biol* 1999, 77(5):420-427.

---

What is claimed is:

1. A method for screening a candidate substance as a candidate for treating rheumatoid arthritis, which comprises the steps of:
   (a) contacting a cell containing an MLN 51 (metastatic lymph node 51) gene or protein with a candidate substance to be analyzed, wherein the cell is a rheumatoid arthritis fibroblast-like synoviocyte; and
   (b) measuring the expression level of the MLN 51 gene, an amount of the MLN 51 protein, or an activity of the MLN 51 protein, wherein detection of a decrease in the expression level of the MLN 51 gene, the amount of the MLN 51 protein, or the activity of the MLN 51 protein compared to a control indicates that the candidate substance is a candidate for treating rheumatoid arthritis.

2. A method for detecting rheumatoid arthritis in a subject, which comprises the steps of:
   (a) contacting a nucleic acid sample obtained from a fibroblast-like synoviocyte of the subject to a probe having a nucleotide sequence complementary to the nucleotide sequence of the MLN 51 (metastatic lymph node 51) gene as set forth in SEQ ID NO:1; wherein the probe has a label that can produce a measurable signal; and
   (b) detecting a level of a hybridization complex of the probe and the nucleic acid sample by measuring the signal from the probe;
   wherein an increase in the level detected compared to a control level indicates that the subject suffers from or is at risk of developing rheumatoid arthritis.

3. A method for detecting rheumatoid arthritis in a subject, which comprises the steps of:
   (a) amplifying a nucleic acid sample obtained from a fibroblast-like synoviocyte of the subject with a primer having a nucleotide sequence complementary to the nucleotide sequence of the MLN 51 (metastatic lymph node 51) gene as set forth in SEQ ID NO:1; and
   (b) detecting an amount of the amplified nucleic acid;
   wherein an increase in the amount of the amplified nucleic acid detected compared to an amount of a similarly amplified control indicates that the subject suffers from or is at risk of developing rheumatoid arthritis.

4. A method for detecting rheumatoid arthritis in a subject, which comprises the steps of:
   (a) contacting a biosample obtained from a fibroblast-like synoviocyte of the subject with an antibody that specifically binds to the MLN 51 (metastatic lymph node 51) protein as set forth in SEQ ID NO:2;
   (b) separating a MLN 51 protein-antibody complex from unbound antibody and MLN 51 protein by washing;
   (c) detecting a level of the MLN 51 protein and antibody complex;
   wherein an increase in the level detected compared to a control level indicates that the subject suffers from or is at risk of developing rheumatoid arthritis.

* * * * *

SEQUENCE LISTING

```
<160> NUMBER OF SEQ ID NOS: 12

<210> SEQ ID NO 1
<211> LENGTH: 4119
<212> TYPE: DNA
<213> ORGANISM: Homo sapiens
<220> FEATURE:
<221> NAME/KEY: CDS
<222> LOCATION: (234)..(2342)

<400> SEQUENCE: 1
gaattccgtt gctgtcgcac acacacacac acacacacac acacccaac acacacacac      60 acacccaac  acacacacac acacacacac acacacacac acacacacac acacagcggg    120
atggccgagc gccgcacgcg tagcacgccg ggactagcta tccagcctcc cagcagcctc    180
tgcgacgggc gcggtgcgta agtacctcgc cggtggtggc cgttctccgt aag atg       236
                                                           Met
                                                            1 gcg gac cgg cgg cgg cag cgc gct tcg caa gac acc gag gac gag gaa      284
Ala Asp Arg Arg Arg Gln Arg Ala Ser Gln Asp Thr Glu Asp Glu Glu
         5                  10                  15 tct ggt gct tcg ggc tcc gac agc ggc ggc tcc ccg ttg cgg gga ggc      332
Ser Gly Ala Ser Gly Ser Asp Ser Gly Gly Ser Pro Leu Arg Gly Gly
     20                  25                  30 ggg agc tgc agc ggt agc gcc gga ggc ggc ggc agc ggc tct ctg cct      380
Gly Ser Cys Ser Gly Ser Ala Gly Gly Gly Gly Ser Gly Ser Leu Pro
 35                  40                  45 tca cag cgc gga ggc cga acc ggg gcc ctt cat ctg cgg cgg gtg gag      428
Ser Gln Arg Gly Gly Arg Thr Gly Ala Leu His Leu Arg Arg Val Glu
 50                  55                  60                  65 agc ggg ggc gcc aag agt gct gag gag tcg gag tgt gag agt gaa gat      476
Ser Gly Gly Ala Lys Ser Ala Glu Glu Ser Glu Cys Glu Ser Glu Asp
                 70                  75                  80 ggc att gaa ggt gat gct gtt ctc tcg gat tat gaa agt gca gaa gac      524
Gly Ile Glu Gly Asp Ala Val Leu Ser Asp Tyr Glu Ser Ala Glu Asp
             85                  90                  95 tcg gaa ggt gaa gaa ggt gaa tac agt gaa gag gaa aac tcc aaa gtg      572
Ser Glu Gly Glu Glu Gly Glu Tyr Ser Glu Glu Glu Asn Ser Lys Val
        100                 105                 110 gag ctg aaa tca gaa gct aat gat gct gtt aat tct tca aca aaa gaa      620
Glu Leu Lys Ser Glu Ala Asn Asp Ala Val Asn Ser Ser Thr Lys Glu
    115                 120                 125 gag aag gga gaa gaa aag cct gac acc aaa agc act gtg act gga gag      668
Glu Lys Gly Glu Glu Lys Pro Asp Thr Lys Ser Thr Val Thr Gly Glu
130                 135                 140                 145 agg caa agt ggg gac gga cag gag agc aca gag cct gtg gag aac aaa      716
Arg Gln Ser Gly Asp Gly Gln Glu Ser Thr Glu Pro Val Glu Asn Lys
                150                 155                 160
```

```
gtg ggt aaa aag ggc cct aag cat ttg gat gat gat gaa gat cgg aag    764
Val Gly Lys Lys Gly Pro Lys His Leu Asp Asp Asp Glu Asp Arg Lys
            165             170                 175 aat cca gca tac ata cct cgg aaa ggg ctc ttc ttt gag cat gat ctt    812
Asn Pro Ala Tyr Ile Pro Arg Lys Gly Leu Phe Phe Glu His Asp Leu
        180                 185                 190 cga ggg caa act cag gag gag gaa gtc aga ccc aag ggg cgt cag cga    860
Arg Gly Gln Thr Gln Glu Glu Glu Val Arg Pro Lys Gly Arg Gln Arg
    195                 200                 205 aag cta tgg aag gat gag ggt cgc tgg gag cat gac aag ttc cgg gaa    908
Lys Leu Trp Lys Asp Glu Gly Arg Trp Glu His Asp Lys Phe Arg Glu
210                 215                 220                 225 gat gag cag gcc cca aag tcc cga cag gag ctc att gct ctt tat ggt    956
Asp Glu Gln Ala Pro Lys Ser Arg Gln Glu Leu Ile Ala Leu Tyr Gly
                230                 235                 240 tat gac att cgc tca gct cat aat cct gat gac atc aaa cct cga aga    1004
Tyr Asp Ile Arg Ser Ala His Asn Pro Asp Asp Ile Lys Pro Arg Arg
            245                 250                 255 atc cgg aaa ccc cga tat ggg agt cct cca caa aga gat cca aac tgg    1052
Ile Arg Lys Pro Arg Tyr Gly Ser Pro Pro Gln Arg Asp Pro Asn Trp
        260                 265                 270 aac ggt gag cgg cta aac aag tct cat cgc cac cag ggt ctt ggg ggc    1100
Asn Gly Glu Arg Leu Asn Lys Ser His Arg His Gln Gly Leu Gly Gly
    275                 280                 285 acc cta cca cca agg aca ttt att aac agg aat gct gca ggt acc ggc    1148
Thr Leu Pro Pro Arg Thr Phe Ile Asn Arg Asn Ala Ala Gly Thr Gly
290                 295                 300                 305 cgt atg tct gca ccc agg aat tat tct cga tct ggg ggc ttc aag gaa    1196
Arg Met Ser Ala Pro Arg Asn Tyr Ser Arg Ser Gly Gly Phe Lys Glu
                310                 315                 320 ggt cgt gct ggt ttt agg cct gtg gaa gct ggt ggg cag cat ggt ggc    1244
Gly Arg Ala Gly Phe Arg Pro Val Glu Ala Gly Gly Gln His Gly Gly
            325                 330                 335 cgg tct ggt gag act gtt aag cat gag att agt tac cgg tca cgg cgc    1292
Arg Ser Gly Glu Thr Val Lys His Glu Ile Ser Tyr Arg Ser Arg Arg
        340                 345                 350 cta gag cag act tct gtg agg gat cca tct cca gaa gca gat gct cca    1340
Leu Glu Gln Thr Ser Val Arg Asp Pro Ser Pro Glu Ala Asp Ala Pro
    355                 360                 365 gtg ctt ggc agt cct gag aag gaa gag gca gcc tca gag cca cca gct    1388
Val Leu Gly Ser Pro Glu Lys Glu Glu Ala Ala Ser Glu Pro Pro Ala
370                 375                 380                 385 gct gct cct gat gct gca cca cca ccc cct gat agg ccc att gag aag    1436
Ala Ala Pro Asp Ala Ala Pro Pro Pro Pro Asp Arg Pro Ile Glu Lys
                390                 395                 400 aaa tcc tat tcc cgg gca aga aga act cga acc aaa gtt gga gat gca    1484
Lys Ser Tyr Ser Arg Ala Arg Arg Thr Arg Thr Lys Val Gly Asp Ala
            405                 410                 415 gtc aag ctt gca gag gag gtg ccc cct cct cct gaa gga ctg att cca    1532
Val Lys Leu Ala Glu Glu Val Pro Pro Pro Pro Glu Gly Leu Ile Pro
        420                 425                 430 gca cct cca gtc cca gaa acc acc cca act cca cct act aag act ggg    1580
Ala Pro Pro Val Pro Glu Thr Thr Pro Thr Pro Pro Thr Lys Thr Gly
    435                 440                 445 acc tgg gaa gct ccg gtg gat tct agt aca agt gga ctt gag caa gat    1628
Thr Trp Glu Ala Pro Val Asp Ser Ser Thr Ser Gly Leu Glu Gln Asp
450                 455                 460                 465 gtg gca caa cta aat ata gca gaa cag aat tgg agt ccg ggg cag cct    1676
Val Ala Gln Leu Asn Ile Ala Glu Gln Asn Trp Ser Pro Gly Gln Pro
                470                 475                 480
```

| | | | | | | | | | | | | | | |
|---|---|---|---|---|---|---|---|---|---|---|---|---|---|---|
| tct | ttc | ctg | caa | cca | cgg | gaa | ctt | cga | ggt | atg | ccc | aac | cat | ata cac | 1724 |
| Ser | Phe | Leu | Gln | Pro | Arg | Glu | Leu | Arg | Gly | Met | Pro | Asn | His | Ile His |
| | | | 485 | | | | | 490 | | | | | 495 | |
| atg | gga | gca | gga | cct | cca | cct | cag | ttt | aac | cgg | atg | gaa | gaa | atg ggt | 1772 |
| Met | Gly | Ala | Gly | Pro | Pro | Pro | Gln | Phe | Asn | Arg | Met | Glu | Glu | Met Gly |
| | | | 500 | | | | | 505 | | | | | 510 | |
| gtc | cag | ggt | ggt | cga | gcc | aaa | cgc | tat | tca | tcc | cag | cgg | caa | aga cct | 1820 |
| Val | Gln | Gly | Gly | Arg | Ala | Lys | Arg | Tyr | Ser | Ser | Gln | Arg | Gln | Arg Pro |
| 515 | | | | | 520 | | | | | 525 | | | | |
| gtg | cca | gag | ccc | ccc | gcc | cct | cca | gtg | cat | atc | agt | atc | atg | gag gga | 1868 |
| Val | Pro | Glu | Pro | Pro | Ala | Pro | Pro | Val | His | Ile | Ser | Ile | Met | Glu Gly |
| 530 | | | | 535 | | | | | 540 | | | | | 545 |
| cat | tac | tat | gat | cca | ctg | cag | ttc | cag | gga | cca | atc | tat | acc | cat ggt | 1916 |
| His | Tyr | Tyr | Asp | Pro | Leu | Gln | Phe | Gln | Gly | Pro | Ile | Tyr | Thr | His Gly |
| | | | 550 | | | | | 555 | | | | | 560 | |
| gac | agc | cct | gcc | ccg | ctg | cct | cca | cag | ggc | atg | ctt | gtg | cag | cca gga | 1964 |
| Asp | Ser | Pro | Ala | Pro | Leu | Pro | Pro | Gln | Gly | Met | Leu | Val | Gln | Pro Gly |
| | | | 565 | | | | | 570 | | | | | 575 | |
| atg | aac | ctt | ccc | cac | cca | ggt | tta | cat | ccc | cac | cag | aca | cca | gct cct | 2012 |
| Met | Asn | Leu | Pro | His | Pro | Gly | Leu | His | Pro | His | Gln | Thr | Pro | Ala Pro |
| | | | 580 | | | | | 585 | | | | | 590 | |
| ctg | ccc | aat | cca | ggc | ctc | tat | ccc | cca | cca | gtg | tcc | atg | tct | cca gga | 2060 |
| Leu | Pro | Asn | Pro | Gly | Leu | Tyr | Pro | Pro | Pro | Val | Ser | Met | Ser | Pro Gly |
| 595 | | | | | 600 | | | | | 605 | | | | |
| cag | cca | cca | cct | cag | cag | ttg | ctt | gct | cct | act | tac | ttt | tct | gct cca | 2108 |
| Gln | Pro | Pro | Pro | Gln | Gln | Leu | Leu | Ala | Pro | Thr | Tyr | Phe | Ser | Ala Pro |
| 610 | | | | | 615 | | | | | 620 | | | | 625 |
| ggc | gtc | atg | aac | ttt | ggt | aat | ccc | agt | tac | cct | tat | gct | cca | ggg gca | 2156 |
| Gly | Val | Met | Asn | Phe | Gly | Asn | Pro | Ser | Tyr | Pro | Tyr | Ala | Pro | Gly Ala |
| | | | 630 | | | | | 635 | | | | | 640 | |
| ctg | cct | ccc | cca | cca | ccg | cct | cat | ctg | tat | cct | aat | aca | cag | gcc cca | 2204 |
| Leu | Pro | Pro | Pro | Pro | Pro | Pro | His | Leu | Tyr | Pro | Asn | Thr | Gln | Ala Pro |
| | | | 645 | | | | | 650 | | | | | 655 | |
| tca | cag | gta | tat | gga | gga | gtg | acc | tac | tat | aac | ccc | gcc | cag | cag cag | 2252 |
| Ser | Gln | Val | Tyr | Gly | Gly | Val | Thr | Tyr | Tyr | Asn | Pro | Ala | Gln | Gln Gln |
| | | | 660 | | | | | 665 | | | | | 670 | |
| gtg | cag | cca | aag | ccc | tcc | cca | ccc | cgg | agg | act | ccc | cag | cca | gtc acc | 2300 |
| Val | Gln | Pro | Lys | Pro | Ser | Pro | Pro | Arg | Arg | Thr | Pro | Gln | Pro | Val Thr |
| 675 | | | | | 680 | | | | | 685 | | | | | |
| atc | aag | ccc | cct | cca | cct | gag | gtt | gta | agc | agg | ggt | tcc | agt | | 2342 |
| Ile | Lys | Pro | Pro | Pro | Pro | Glu | Val | Val | Ser | Arg | Gly | Ser | Ser | |
| 690 | | | | | 695 | | | | | 700 | | | | | |
| taatacaagt | ttctgaatat | tttaaatctt | aacatcatat | aaaaagcagc | agaggtgaga | | | | | | | | | | 2402 |
| actcagaaga | gaaatacagc | tggctatcta | ctaccagaag | ggcttcaaag | atatagggtg | | | | | | | | | | 2462 |
| tggctcctac | cagcaaacag | ctgaaagagg | aggacccctg | ccttcctctg | aggacaggct | | | | | | | | | | 2522 |
| ctagagagag | ggagaaacaa | gtggacctcg | tcccatcttc | actcttcact | tgagttggct | | | | | | | | | | 2582 |
| gtgttcgggg | gagcagagag | agccagacag | ccccaagctt | ctgagtctag | atacagaagc | | | | | | | | | | 2642 |
| ccatgtcttc | tgctgttctt | cacttctggg | aaattgaagt | gtcttctgtt | cccaaggaag | | | | | | | | | | 2702 |
| ctccttcctg | tttgttttgt | tttctaagat | gttcatttt | aaagcctggc | ttcttatcct | | | | | | | | | | 2762 |
| taatattatt | ttaatttttt | ctctttgttt | ctgtttcttg | ctctctctcc | ctgcctttaa | | | | | | | | | | 2822 |
| atgaaacaag | tctagtcttc | tggttttcta | gcccctctgg | attcccttt | gactcttccg | | | | | | | | | | 2882 |
| tgcatcccag | ataatggaga | atgtatcagc | cagccttccc | caccaagtct | aaaaagacct | | | | | | | | | | 2942 |
| ggcctttcac | ttttagttgg | catttgttat | cctcttgtat | acttgtattc | ccttaactct | | | | | | | | | | 3002 |
| aaccctgtgg | aagcatggct | gtctgcacag | agggtcccat | tgtgcagaaa | agctcagagt | | | | | | | | | | 3062 |

```
aggtgggtag gagcccttct ctttgactta ggttttagg agtctgagca tccatcaata    3122
cctgtactat gatgggcttc tgttctctgc tgagggccaa taccctactg tggggagaga    3182
tggcacacca gatgcttttg tgagaaaggg atggtggagt gagagccttt gcctttaggg    3242
gtgtgtattc acatagtcct cagggctcag tcttttgagg taagtggaat tagagggcct    3302
tgcttctctt ctttccattc ttcttgctac accccttttc cagttgctgt ggaccaatgc    3362
atctctttaa aggcaaatat tatccagcaa gcagtctacc ctgtcctttg caattgctct    3422
tctccacgtc tttcctgcta caagtgtttt agatgttact accttatttt ccccgaattc    3482 tattttgtc cttgcagaca gaatataaaa actcctgggc ttaaggccta aggaagccag    3542 tcacttctg ggcaagggct cctatctttc ctccctatcc atggcactaa accacttctc    3602
tgctgcctct gtggaagaga ttcctattac tgcagtacat acgtctgcca ggggtaacct    3662
ggccactgtc cctgtccttc tacagaacct gagggcaaag atggtggctg tgtctctccc    3722
cggtaatgtc actgttttta ttccttccat ctagcagctg gcctaatcac tctgagtcac    3782
aggtgtggga tggagagtgg ggagaggcac ttaatctgta accccaagg aggaaataac    3842 taagagattc ttctaggggt agctggtggt tgtgcctttt gtaggctgtt cccttttgcct    3902 taaacctgaa gatgtctcct caagcctgtg ggcagcatgc ccagattccc agaccttaag    3962
acactgtgag agttgtctct gttggtccac tgtgtttagt tgcaaggatt tttccatgtg    4022
tggtggtgtt ttttgttact gttttaaagg gtgcccattt gtgatcagca ttgtgacttg    4082
gagataataa aatttagact ataaacttga aaaaaaa                            4119
```

<210> SEQ ID NO 2
<211> LENGTH: 703
<212> TYPE: PRT
<213> ORGANISM: Homo sapiens

<400> SEQUENCE: 2

```
Met Ala Asp Arg Arg Gln Arg Ala Ser Gln Asp Thr Glu Asp Glu
1               5                   10                  15

Glu Ser Gly Ala Ser Gly Ser Asp Ser Gly Gly Ser Pro Leu Arg Gly
            20                  25                  30

Gly Gly Ser Cys Ser Gly Ser Ala Gly Gly Gly Ser Gly Ser Leu
        35                  40                  45

Pro Ser Gln Arg Gly Gly Arg Thr Gly Ala Leu His Leu Arg Arg Val
    50                  55                  60

Glu Ser Gly Gly Ala Lys Ser Ala Glu Glu Ser Cys Glu Ser Glu
65                  70                  75                  80

Asp Gly Ile Glu Gly Asp Ala Val Leu Ser Asp Tyr Glu Ser Ala Glu
                85                  90                  95

Asp Ser Glu Gly Glu Glu Gly Glu Tyr Ser Glu Glu Asn Ser Lys
            100                 105                 110

Val Glu Leu Lys Ser Glu Ala Asn Asp Ala Val Asn Ser Ser Thr Lys
        115                 120                 125

Glu Glu Lys Gly Glu Glu Lys Pro Asp Thr Lys Ser Thr Val Thr Gly
    130                 135                 140

Glu Arg Gln Ser Gly Asp Gly Gln Glu Ser Thr Glu Pro Val Glu Asn
145                 150                 155                 160

Lys Val Gly Lys Lys Gly Pro Lys His Leu Asp Asp Glu Asp Arg
                165                 170                 175

Lys Asn Pro Ala Tyr Ile Pro Arg Lys Gly Leu Phe Phe Glu His Asp
            180                 185                 190
```

```
Leu Arg Gly Gln Thr Gln Glu Glu Val Arg Pro Lys Gly Arg Gln
        195                 200                 205

Arg Lys Leu Trp Lys Asp Glu Gly Arg Trp Glu His Asp Lys Phe Arg
    210                 215                 220

Glu Asp Glu Gln Ala Pro Lys Ser Arg Gln Glu Leu Ile Ala Leu Tyr
225                 230                 235                 240

Gly Tyr Asp Ile Arg Ser Ala His Asn Pro Asp Asp Ile Lys Pro Arg
                245                 250                 255

Arg Ile Arg Lys Pro Arg Tyr Gly Ser Pro Pro Gln Arg Asp Pro Asn
            260                 265                 270

Trp Asn Gly Glu Arg Leu Asn Lys Ser His Arg His Gln Gly Leu Gly
        275                 280                 285

Gly Thr Leu Pro Pro Arg Thr Phe Ile Asn Arg Asn Ala Ala Gly Thr
    290                 295                 300

Gly Arg Met Ser Ala Pro Arg Asn Tyr Ser Arg Ser Gly Gly Phe Lys
305                 310                 315                 320

Glu Gly Arg Ala Gly Phe Arg Pro Val Glu Ala Gly Gly Gln His Gly
                325                 330                 335

Gly Arg Ser Gly Glu Thr Val Lys His Glu Ile Ser Tyr Arg Ser Arg
            340                 345                 350

Arg Leu Glu Gln Thr Ser Val Arg Asp Pro Ser Pro Glu Ala Asp Ala
        355                 360                 365

Pro Val Leu Gly Ser Pro Glu Lys Glu Ala Ala Ser Glu Pro Pro
    370                 375                 380

Ala Ala Ala Pro Asp Ala Ala Pro Pro Pro Asp Arg Pro Ile Glu
385                 390                 395                 400

Lys Lys Ser Tyr Ser Arg Ala Arg Arg Thr Arg Thr Lys Val Gly Asp
                405                 410                 415

Ala Val Lys Leu Ala Glu Glu Val Pro Pro Pro Glu Gly Leu Ile
            420                 425                 430

Pro Ala Pro Pro Val Pro Glu Thr Thr Pro Thr Pro Thr Lys Thr
    435                 440                 445

Gly Thr Trp Glu Ala Pro Val Asp Ser Ser Thr Ser Gly Leu Glu Gln
    450                 455                 460

Asp Val Ala Gln Leu Asn Ile Ala Glu Gln Asn Trp Ser Pro Gly Gln
465                 470                 475                 480

Pro Ser Phe Leu Gln Pro Arg Glu Leu Arg Gly Met Pro Asn His Ile
                485                 490                 495

His Met Gly Ala Gly Pro Pro Gln Phe Asn Arg Met Glu Glu Met
            500                 505                 510

Gly Val Gln Gly Gly Arg Ala Lys Arg Tyr Ser Ser Gln Arg Gln Arg
        515                 520                 525

Pro Val Pro Glu Pro Pro Ala Pro Pro Val His Ile Ser Ile Met Glu
    530                 535                 540

Gly His Tyr Tyr Asp Pro Leu Gln Phe Gln Gly Pro Ile Tyr Thr His
545                 550                 555                 560

Gly Asp Ser Pro Ala Pro Leu Pro Pro Gln Gly Met Leu Val Gln Pro
                565                 570                 575

Gly Met Asn Leu Pro His Pro Gly Leu His Pro His Gln Thr Pro Ala
            580                 585                 590

Pro Leu Pro Asn Pro Gly Leu Tyr Pro Pro Val Ser Met Ser Pro
    595                 600                 605

Gly Gln Pro Pro Pro Gln Gln Leu Leu Ala Pro Thr Tyr Phe Ser Ala
```

```
                    610                 615                 620
Pro Gly Val Met Asn Phe Gly Asn Pro Ser Tyr Pro Tyr Ala Pro Gly
625                 630                 635                 640

Ala Leu Pro Pro Pro Pro Pro His Leu Tyr Pro Asn Thr Gln Ala
            645                 650                 655

Pro Ser Gln Val Tyr Gly Val Thr Tyr Tyr Asn Pro Ala Gln Gln
                660                 665                 670

Gln Val Gln Pro Lys Pro Ser Pro Pro Arg Arg Thr Pro Gln Pro Val
                    675                 680                 685

Thr Ile Lys Pro Pro Pro Glu Val Val Ser Arg Gly Ser Ser
            690                 695                 700

<210> SEQ ID NO 3
<211> LENGTH: 703
<212> TYPE: PRT
<213> ORGANISM: Homo sapiens

<400> SEQUENCE: 3

Met Ala Asp Arg Arg Gln Arg Ala Ser Gln Asp Thr Glu Asp Glu
1               5                   10                  15

Glu Ser Gly Ala Ser Gly Ser Asp Gly Gly Ser Pro Leu Arg Gly
                20                  25                  30

Gly Gly Ser Cys Ser Gly Ser Ala Gly Gly Gly Ser Gly Ser Leu
            35                  40                  45

Pro Ser Gln Arg Gly Gly Arg Thr Gly Ala Leu His Leu Arg Arg Val
                50                  55                  60

Glu Ser Gly Gly Ala Lys Ser Ala Glu Glu Ser Glu Cys Glu Ser Glu
65                  70                  75                  80

Asp Gly Ile Glu Gly Asp Ala Val Leu Ser Asp Tyr Glu Ser Ala Glu
                85                  90                  95

Asp Ser Glu Gly Glu Glu Gly Glu Tyr Ser Glu Glu Glu Asn Ser Lys
                100                 105                 110

Val Glu Leu Lys Ser Glu Ala Asn Asp Ala Val Asn Ser Ser Thr Lys
            115                 120                 125

Glu Glu Lys Gly Glu Glu Lys Pro Asp Thr Lys Ser Thr Val Thr Gly
        130                 135                 140

Glu Arg Gln Ser Gly Asp Gly Gln Glu Ser Thr Glu Pro Val Glu Asn
145                 150                 155                 160

Lys Val Gly Lys Lys Gly Pro Lys His Leu Asp Asp Asp Glu Asp Arg
                165                 170                 175

Lys Asn Pro Ala Tyr Ile Pro Arg Lys Gly Leu Phe Phe Glu His Asp
                180                 185                 190

Leu Arg Gly Gln Thr Gln Glu Glu Val Arg Pro Lys Gly Arg Gln
            195                 200                 205

Arg Lys Leu Trp Lys Asp Glu Gly Arg Trp Glu His Asp Lys Phe Arg
210                 215                 220

Glu Asp Glu Gln Ala Pro Lys Ser Arg Gln Glu Leu Ile Ala Leu Tyr
225                 230                 235                 240

Gly Tyr Asp Ile Arg Ser Ala His Asn Pro Asp Asp Ile Lys Pro Arg
                245                 250                 255

Arg Ile Arg Lys Pro Arg Tyr Gly Ser Pro Pro Gln Arg Asp Pro Asn
            260                 265                 270

Trp Asn Gly Glu Arg Leu Asn Lys Ser His Arg His Gln Gly Leu Gly
                275                 280                 285

Gly Thr Leu Pro Pro Arg Thr Phe Ile Asn Arg Asn Ala Ala Gly Thr
```

```
                  290                 295                 300
Gly Arg Met Ser Ala Pro Arg Asn Tyr Ser Arg Ser Gly Gly Phe Lys
305                 310                 315                 320

Glu Gly Arg Ala Gly Phe Arg Pro Val Glu Ala Gly Gly Gln His Gly
                325                 330                 335

Gly Arg Ser Gly Glu Thr Val Lys His Glu Ile Ser Tyr Arg Ser Arg
            340                 345                 350

Arg Leu Glu Gln Thr Ser Val Arg Asp Pro Ser Pro Glu Ala Asp Ala
        355                 360                 365

Pro Val Leu Gly Ser Pro Glu Lys Glu Ala Ser Glu Pro Pro
370                 375                 380

Ala Ala Ala Pro Asp Ala Ala Pro Pro Pro Asp Arg Pro Ile Glu
385                 390                 395                 400

Lys Lys Ser Tyr Ser Arg Ala Arg Arg Thr Arg Thr Lys Val Gly Asp
                405                 410                 415

Ala Val Lys Leu Ala Glu Glu Val Pro Pro Pro Glu Gly Leu Ile
            420                 425                 430

Pro Ala Pro Pro Val Pro Glu Thr Thr Pro Thr Pro Thr Lys Thr
        435                 440                 445

Gly Thr Trp Glu Ala Pro Val Asp Ser Ser Thr Ser Gly Leu Glu Gln
450                 455                 460

Asp Val Ala Gln Leu Asn Ile Ala Glu Gln Asn Trp Ser Pro Gly Gln
465                 470                 475                 480

Pro Ser Phe Leu Gln Pro Arg Glu Leu Arg Gly Met Pro Asn His Ile
                485                 490                 495

His Met Gly Ala Gly Pro Pro Gln Phe Asn Arg Met Glu Glu Met
            500                 505                 510

Gly Val Gln Gly Gly Arg Ala Lys Arg Tyr Ser Ser Gln Arg Gln Arg
        515                 520                 525

Pro Val Pro Glu Pro Pro Ala Pro Pro Val His Ile Ser Ile Met Glu
530                 535                 540

Gly His Tyr Tyr Asp Pro Leu Gln Phe Gln Gly Pro Ile Tyr Thr His
545                 550                 555                 560

Gly Asp Ser Pro Ala Pro Leu Pro Pro Gln Gly Met Leu Val Gln Pro
                565                 570                 575

Gly Met Asn Leu Pro His Pro Gly Leu His Pro His Gln Thr Pro Ala
            580                 585                 590

Pro Leu Pro Asn Pro Gly Leu Tyr Pro Pro Val Ser Met Ser Pro
        595                 600                 605

Gly Gln Pro Pro Pro Gln Gln Leu Leu Ala Pro Thr Tyr Phe Ser Ala
610                 615                 620

Pro Gly Val Met Asn Phe Gly Asn Pro Ser Tyr Pro Tyr Ala Pro Gly
625                 630                 635                 640

Ala Leu Pro Pro Pro Pro Pro His Leu Tyr Pro Asn Thr Gln Ala
                645                 650                 655

Pro Ser Gln Val Tyr Gly Gly Val Thr Tyr Tyr Asn Pro Ala Gln Gln
            660                 665                 670

Gln Val Gln Pro Lys Pro Ser Pro Arg Arg Thr Pro Gln Pro Val
        675                 680                 685

Thr Ile Lys Pro Pro Pro Glu Val Val Ser Arg Gly Ser Ser
690                 695                 700

<210> SEQ ID NO 4
<211> LENGTH: 22
```

```
<212> TYPE: DNA
<213> ORGANISM: Artificial Sequence
<220> FEATURE:
<223> OTHER INFORMATION: primer for MLN 51 gene

<400> SEQUENCE: 4
aagacaccga ggacgaggaa tc                                          22

<210> SEQ ID NO 5
<211> LENGTH: 22
<212> TYPE: DNA
<213> ORGANISM: Artificial Sequence
<220> FEATURE:
<223> OTHER INFORMATION: primer for MLN 51 gene

<400> SEQUENCE: 5
ccttccatag ctttcgctga cg                                          22

<210> SEQ ID NO 6
<211> LENGTH: 42
<212> TYPE: DNA
<213> ORGANISM: Artificial Sequence
<220> FEATURE:
<223> OTHER INFORMATION: siRNA for MLN 51 gene

<400> SEQUENCE: 6
taatacgact cactataggg tactcgtaag atggcggacc gg                    42

<210> SEQ ID NO 7
<211> LENGTH: 39
<212> TYPE: DNA
<213> ORGANISM: Artificial Sequence
<220> FEATURE:
<223> OTHER INFORMATION: siRNA for MLN 51 gene

<400> SEQUENCE: 7
taatacgact cactataggg tccgtcccca ctttgcctc                        39

<210> SEQ ID NO 8
<211> LENGTH: 22
<212> TYPE: DNA
<213> ORGANISM: Artificial Sequence
<220> FEATURE:
<223> OTHER INFORMATION: primer for mMLN 51 gene

<400> SEQUENCE: 8
tccctgccct gccctgactt ta                                          22

<210> SEQ ID NO 9
<211> LENGTH: 22
<212> TYPE: DNA
<213> ORGANISM: Artificial Sequence
<220> FEATURE:
<223> OTHER INFORMATION: reverse primer for mMLN51 gene

<400> SEQUENCE: 9
cctcgcgtgc tgtgggaact ct                                          22

<210> SEQ ID NO 10
<211> LENGTH: 19
<212> TYPE: DNA
<213> ORGANISM: Artificial Sequence
<220> FEATURE:
<223> OTHER INFORMATION: Forward Primer for GAPDH

<400> SEQUENCE: 10
ccacagtcca tgccatcac                                              19
```

```
<210> SEQ ID NO 11
<211> LENGTH: 20
<212> TYPE: DNA
<213> ORGANISM: Artificial Sequence
<220> FEATURE:
<223> OTHER INFORMATION: Reverse Primer for GAPDH

<400> SEQUENCE: 11
tccaccaccc tgttgctgta                                                    20

<210> SEQ ID NO 12
<211> LENGTH: 42
<212> TYPE: DNA
<213> ORGANISM: Artificial Sequence
<220> FEATURE:
<223> OTHER INFORMATION: siRNA for mMLN51 gene

<400> SEQUENCE: 12
taatacgact cactataggg tactctgcct ctccccagtc ac                           42
```